(12) United States Patent
Hashman et al.

(10) Patent No.: US 9,932,543 B2
(45) Date of Patent: Apr. 3, 2018

(54) BACTERIAL SPORE COMPOSITIONS FOR INDUSTRIAL USES

(71) Applicant: Envera, LLC, West Chester, PA (US)

(72) Inventors: Tommie Eugene Hashman, West Chester, PA (US); Michael Matheny, West Chester, PA (US)

(73) Assignee: Envera, LLC, West Chester, PA (US)

(*) Notice: Subject to any disclaimer, the term of this patent is extended or adjusted under 35 U.S.C. 154(b) by 0 days.

(21) Appl. No.: 14/819,583

(22) Filed: Aug. 6, 2015

(65) Prior Publication Data

US 2016/0040119 A1    Feb. 11, 2016

Related U.S. Application Data

(60) Provisional application No. 62/033,825, filed on Aug. 6, 2014.

(51) Int. Cl.

| | | |
|---|---|---|
| *C11D 3/22* | (2006.01) | |
| *C05F 11/08* | (2006.01) | |
| *A01N 25/00* | (2006.01) | |
| *A61K 35/742* | (2015.01) | |
| *A61K 47/12* | (2006.01) | |
| *B09C 1/10* | (2006.01) | |
| *C02F 3/34* | (2006.01) | |
| *C09K 8/582* | (2006.01) | |
| *C11D 3/33* | (2006.01) | |
| *C11D 3/38* | (2006.01) | |
| *C12N 1/20* | (2006.01) | |
| *C12P 5/02* | (2006.01) | |
| *C02F 11/04* | (2006.01) | |
| *A01N 63/02* | (2006.01) | |
| *A23K 10/12* | (2016.01) | |
| *A23K 10/18* | (2016.01) | |
| *A23K 50/75* | (2016.01) | |
| *A23K 50/80* | (2016.01) | |
| *A01N 63/00* | (2006.01) | |
| *A61K 35/00* | (2006.01) | |

(52) U.S. Cl.
CPC ............ *C11D 3/221* (2013.01); *A01N 25/00* (2013.01); *A01N 63/00* (2013.01); *A01N 63/02* (2013.01); *A23K 10/12* (2016.05); *A23K 10/18* (2016.05); *A23K 50/75* (2016.05); *A23K 50/80* (2016.05); *A61K 35/742* (2013.01); *A61K 47/12* (2013.01); *B09C 1/10* (2013.01); *B09C 1/105* (2013.01); *C02F 3/34* (2013.01); *C02F 3/348* (2013.01); *C02F 11/04* (2013.01); *C05F 11/08* (2013.01); *C09K 8/582* (2013.01); *C11D 3/33* (2013.01); *C11D 3/381* (2013.01); *C12N 1/20* (2013.01); *C12P 5/023* (2013.01); *A61K 2035/115* (2013.01); *B09C 2101/00* (2013.01); *Y02E 50/343* (2013.01); *Y02W 10/23* (2015.05); *Y02W 30/47* (2015.05)

(58) Field of Classification Search
None
See application file for complete search history.

(56) References Cited

U.S. PATENT DOCUMENTS

| | | |
|---|---|---|
| 5,062,956 A | 11/1991 | Lupton et al. |
| 5,681,739 A | 10/1997 | Turick et al. |
| 2002/0090697 A1 | 7/2002 | Hince |
| 2005/0096225 A1 | 5/2005 | Johnson |
| 2006/0134765 A1* | 6/2006 | Saha .................. C12P 7/18 435/158 |
| 2011/0033436 A1 | 2/2011 | Chen et al. |
| 2011/0154544 A1 | 6/2011 | Riggs |
| 2013/0164398 A1* | 6/2013 | Farmer ............... A61K 35/742 424/780 |
| 2014/0112899 A1 | 4/2014 | Jeschke et al. |
| 2014/0295482 A1 | 10/2014 | Lyte |

FOREIGN PATENT DOCUMENTS

| | | |
|---|---|---|
| WO | WO-95/25163 A1 | 9/1995 |
| WO | WO-99/05310 A1 | 2/1999 |
| WO | 02/00035 | 1/2002 |
| WO | WO-2010/069990 A1 | 6/2010 |
| WO | WO-2010/070005 A1 | 6/2010 |
| WO | WO 2012/087980 | 6/2012 |

(Continued)

OTHER PUBLICATIONS

Lalloo et al., "A downstream process for production of a viable and stable Bacillus cereus aquaculture biological agent", Applied Microbiology and Biotechnology 2010, vol. 86, pp. 499-508.*
Hong et al., "The use of bacterial spore formers as probiotics", FEMS Microbiology Reviews 2005, vol. 29, pp. 813-835.*
Cartman, Stephen T., et al., "Bacillus Subtilis Spores Germinate in the Chicken Gastrointestinal Tract", Applied and Environmental Microbiology, Aug. 2008, vol. 74, No. 16, pp. 5254-5258.
Crane, J.M., et al., "Nutrient-Induced Spore Germination of a Bacillus Amyloliquefaciens Biocontrol Agent on Wheat Spikes", Journal of Applied Microbiology, 2014, pp. 1-12.
Foerster, Harold F. et al., "Response of Bacillus Spores to Combinations of Germinative Compounds", Journal of Bacteriology, Mar. 1966, vol. 91, No. 3, pp. 1168-1177.
Foerster, Harold F, et al., "Endotrophic Calcium, Strontium, and Barium Spores of Bacillus Megaterium and Bacillus Cereus", Journal of Bacteriology, Mar. 1966, vol. 91, No. 3, pp. 1333-1345.
Han, Qing-Qing, et al., "Beneficial Soil Bacterium Bacillus Subtilis (GB03) Augments Salt Tolerance of White Clover", Frontiers in Plant Science, Oct. 2014, vol. 5, pp. 1-8.
Zhang, Huiming, et al., "A Soil Bacterium Regulates Plant Acquisition of Iron Via Deficiency-Inducible Mechanisms", The Plant Journal, 2009, vol. 58, pp. 568-577.

(Continued)

*Primary Examiner* — Michelle F. Paguio Frising

(74) *Attorney, Agent, or Firm* — McCarter & English, LLP

(57) ABSTRACT

In one aspect, the present invention is directed to a plant or plant part coated with a composition comprising a bacterial spore and a germinative compound. In another aspect the present invention is directed to a method of enhancing the growth of a plant or plant part comprising coating such plant or plant part with such a composition. In yet another aspect, the present invention is directed to a composition comprising a bacterial spore and a germinative compound where such components are maintained in an inactive form. The present invention also relates to use of the compositions in wastewater treatment, environmental remediation, oil recovery, aquaculture systems, and direct fed microbials.

14 Claims, No Drawings

(56) References Cited

FOREIGN PATENT DOCUMENTS

| WO | WO-2013/067305 A1 | 5/2013 |
|---|---|---|
| WO | 2014/106776 | 7/2014 |
| WO | 2014/193746 | 12/2014 |

OTHER PUBLICATIONS

Xie, Xitao, et al., "Sustained Growth Promotion in Arabidopsis with Long-Term Exposure to the Beneficial Soil Bacterium *Bacillus subtilis* (GB03)", Plant Signaling & Behavior, Oct. 2009, vol. 4, Issue 10, pp. 948-953.

International Search Report and Written Opinion dated Dec. 31, 2015, based on co-pending International Application No. PCT/US2015/043979, filed Aug. 6, 2015.

Russell et al., "Bacterial Spores and Chemical Sporicidal Agents", Clinical Microbiol. Rev., Apr. 1990, vol. 3, No. 2, pp. 99-119.

Atluri et al., Cooperativity Between Different Nutrient Receptors in Germination of Spores of *Bacillus subtilis* and Reduction of This Cooperativity by Alterations in GerB Receptor, Journal of Bacteriology, Jan. 2006, vol. 188, No. 1, pp. 28-36.

Blocher et al., "Inhibition of Germinant Binding by Bacterial Spores in Acidic Environments", Applied and Environmental Microbiology, Aug. 1985, vol. 50, No. 2, pp. 274-279.

Maathuis et al., "Survival and Metabolic Activity of the GanedenBC$^{30}$ Strain of Bacillus Coagulans in a Dynamic in vitro Model of the Stomach and Small Intestine", Beneficial Microbes, 2010, vol. 1, No. 1, pp. 31-36.

Huq et al., "Encapsulation of Probiotic Bacteria in Biopolymeric System", Critical Reviews in Food Science and Nutrition, 2012, pp. 1549-7852.

Bagheri et al., "Growth, Survival and Gut Microbial Load of Rainbow Trout (*Onchorhynchus mykiss*) Fry Given Diet Supplemented with Probiotic during the Two Months of First Feeding", Turkish Journal of Fisheries and Aquatic Systems, 2008, vol. 8, pp. 43-48.

Extended European Search Report for Application No. 14749483.5 dated Sep. 19, 2016.

International Preliminary Report on Patentability for PCT/US2014/015076, dated Apr. 28, 2014.

Yi et al., "Studies of the Commitment Step in the Germination of Spores of *Bacillus* Species", Journal of Bacteriology, 2010, vol. 192, No. 13, pp. 3424-3433.

Paredes-Sabja et al., "Germination of Spores of Bacillales and Clostridiales species: Mechanisms and Protein Involved", Trends in Microbiology, 2011, vol. 19, No. 2, pp. 85-94.

Amberex 695 (AX695-50) Yeast Extract Technical Data Sheet, Oct. 2011.

Supplementary european Search Report, dated Nov. 22, 2017 relating to co-pending European Patent Application No. 15830591.2, filed Aug. 6, 2015—7 Pages.

\* cited by examiner

BACTERIAL SPORE COMPOSITIONS FOR INDUSTRIAL USES

CROSS REFERENCE TO RELATED APPLICATIONS

This application claims the priority benefit of U.S. Provisional Application Ser. No. 62/033,825 filed Aug. 6, 2014, which is hereby incorporated by reference in its entirety.

FIELD OF THE INVENTION

The present invention relates generally to bacterial spore compositions for industrial uses such as agriculture, environmental remediation, composting, methane production, cleaning supplies, oil recovery, and direct fed microbials.

BACKGROUND OF THE INVENTION

Spore-forming bacterial species have a wide range of industrial applications including uses in agriculture, environmental remediation, composting, methane production, oil recovery, and cleaning supplies. Depending upon the particular bacterial species employed, compositions comprising the bacteria may be suitable for agricultural, horticultural, environmental, probiotic, aquatic, industrial and sanitation uses, among others. Several spore-forming bacteria species have utility across many industries. For example, *Bacillus megaterium, Bacillus amyloliquefaciens, Bacillus licheniformis, Bacillus subtilis*, and *Bacillus pumilus* are used as agricultural fungicides, and in wastewater treatment, cleaning products, and direct fed microbials.

Regarding agricultural applications, the use of spore forming bacteria to enhance the health of plants is well known in the art. For example, Zhang et al. (2009, Plant J 58: 568-577) teach that the plant growth promoting bacterium *Bacillus subtilis* GB03 increases iron acquisition by plants and photosynthetic capacity. Xie et al. (2009, Plant Signaling and Behavior 4(10): 948-953) teach that volatiles produced by this same strain of *Bacillus subtilis* increased plant growth and seed count. Han et al. (2014, Frontiers in Plant Science 5(525): 1-8) report that white clover plants grown in *Bacillus subtilis* GB03 inoculated soil were significantly larger than non-inoculated controls with respect to shoot height, root length, plant biomass, leaf area and chlorophyll content. Spores of such bacteria may also be coated onto seeds or other plant propagative material, such that once sown or planted an enhanced environment which supports germination of the seed, stimulation of plant growth or biological protection of the seed and resulting plant can be established. For example, symbiotic bacteria such as those from the genera *Rhizobium* and *Bradyrhizobium*, which enable nitrogen fixation in leguminous plants may be used to inoculate leguminous plants to aid nodule formation. Inoculation can be accomplished by coating seeds, dusting on-farm of seeds or crops or placing inoculate in-furrow at planting time.

Spore forming bacteria may also be used in environmental remediation methods such as bioremediation. Bioremediation involves the use of microorganisms to convert chemical compounds into innocuous or less harmful chemical compounds. Bioremediation technologies generally have lower costs than competing physical technologies, and can be adapted to a broader range of contamination problems and variations in field conditions. See US 2002/0090697.

Contaminated media may be treated with bacteria to promote the biodegradation of organic contaminants in water, soil, and industrial wastes. For example, Lupton et al. (U.S. Pat. No. 5,062,956) discusses a method of removing soluble Cr(VI) using anaerobic bacteria to reduce Cr(VI) to Cr(III) and immobilize the Cr(III) as the insoluble hydroxide which settles out as a solid. Lupton et al. also describes treatment of aqueous residues containing undesirable amounts of Cr(VI) in a continuous bioreactor. Turick et al. (U.S. Pat. No. 5,681,739) describes a method of reducing the concentration of Cr(VI) in a liquid aqueous residue comprising the steps of providing Cr(Vi)-reducing bacteria, mixing the liquid aqueous residue with a nutrient medium (e.g., molasses, acetic acid, amino acids, casamino acids, urea), and contacting the mixture with the anaerobic bacteria to enhance the reduction of Cr(VI) to Cr(III). This process can be used for the bioremediation of hexavalent chromium contaminated soil and/or ground water.

One difficulty associated with the use of such bacteria is that while they must be in their vegetative state to afford such benefits, it is difficult to formulate *Bacillus* species and other spore forming bacteria in their vegetative form such that they will possess an adequate shelf life. In addition *Bacillus* species in their vegetative form may not be able to survive the harsh conditions needed for industrial uses, such as the conditions to which seeds or other plant propagative materials are subjected before conditions suitable for seed germination occur. In contrast, formulations of such species in their spore form are much more suitable for commercial and practical use. For example, as is noted by Cartman et al. (2008, Applied and Environmental Microbiology, August, p. 5254-5258) "[b]acterial spores are particularly well suited for use as live microbial products as they are metabolically dormant and highly resilient to environmental stress. These intrinsic properties are highly desirable from a commercial perspective and mean that spore-based products have a long shelf life and retain their viability during distribution and storage."

The use of certain compounds, particularly certain L-amino acids, to stimulate the germination of *Bacillus* spores has been reported in the literature. For example, Foerster et al. (1996, Journal of Bacteriology 91(3): 1168-1177) discloses that the addition of L-alanine to spore suspensions in aqueous solutions will cause the germination of a number of *Bacillus* species. However one of the challenges in using combinations of bacterial spores and germinative compounds in industrial uses is maintaining the spore in an inactive form in the presence of the germinative compound until germination of the spores is required. For example, a plant propagative material such as a seed treated with a bacterial spore composition may be subjected to a storage period of several months before planting. Thus a need exists for bacterial spore formulations that can stimulate rapid germination of bacterial spores under favorable conditions, but that also prevent premature germination of the spores until germination of the spore is required.

In addition, bacteria for agricultural or industrial use may be exposed to a range of environmental conditions such as low soil pH, high salt concentrations (e.g. NaCl), and high metal concentrations (e.g. copper and aluminum) that are unfavorable for bacterial spore germination. Thus a need exists to develop formulations of bacterial spores that are able to germinate under these adverse conditions.

SUMMARY OF THE INVENTION

In one aspect, the present invention is directed to a plant propagative material coated with a composition comprising a bacterial spore and a germinative compound. In certain embodiments, the spore and the germinative compound are maintained in an inactive form such that the germinative compound will not induce germination of the spore until the composition is subjected to an activation environment. The composition may further comprises a substance which prohibits the bacterial spore and the germinative compound from interacting until the composition is subjected to an activation environment. In certain embodiments, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent. In some embodiments, the composition comprises an intimate mixture of the bacterial spore and the germinative compound, wherein the bacterial spore and the germinative compound are maintained in proximate position until they reach an environment conducive to germination.

In certain embodiments, the plant propagative material is selected from the group consisting of a flower, a seed, a root, a fruit, a tuber, a bulb, a rhizome, a shoot, a sprout, a seed, a leaf, a seedling, and a transplant. In a particular embodiment, the plant propagative material is a seed. The plant propagative material may be transplanted after germination or after emergence from soil.

In certain embodiments of the aforementioned plant propagative materials, the bacterial spore is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus popillae, Bacillus pumilus, Bacillus siamensis, Bacillus simplex, Bacillus sphaericus, Bacillus* spp., *Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and a species of the genus *Streptomyces*.

In certain embodiments of the aforementioned plant propagative materials, the germinative compound is selected from the group consisting of L-alanine, L-valine, L-proline, L-leucine, L-cysteine, L-threonine, L-glutamine, L-asparagine, L-phenylalanine, and analogues thereof. In particular embodiments, the bacterial spore is selected from the group consisting of *B. subtilis, B. amyloliquefaciens, B. firmus, B. licheniformis, B. megaterium*, and *B. pumilus*; and the germinative compound is selected from the group consisting of L-alanine, L-valine and L-asparagine. The composition may further comprise a seed coating polymer. In certain embodiments, the composition further comprises a substance selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In another aspect, the present invention relates to a method of enhancing the growth or yield of a plant propagative material comprising coating the plant propagative material with a composition comprising a bacterial spore and a germinative compound, wherein the growth or yield of the plant propagative material is enhanced relative to the growth or yield of a corresponding plant propagative material that is not coated with said composition. In certain embodiments, the spore and the germinative compound are maintained in an inactive form such that the germinative compound will not induce germination of the spore until the composition is subjected to an activation environment. In some embodiments, the composition further comprises a substance which prohibits the bacterial spore and the germinative compound from interacting until the composition is subjected to an activation environment. In some embodiments, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In certain embodiments of the aforementioned methods, the composition comprises an intimate mixture of the bacterial spore and the germinative compound, wherein the bacterial spore and the germinative compound are maintained in proximate position until they reach an environment conducive to germination. In some embodiments, the plant propagative material is selected from the group consisting of a flower, seed, a root, a fruit, a tuber, a bulb, a rhizome, a shoot, a sprout, a seed, a leaf, a seedling, and a transplant. In particular embodiments, the plant propagative material is a seed. In some embodiments, the methods further comprise transplanting the plant propagative material after germination or after emergence from soil.

In certain embodiments, the bacterial spore used in the aforementioned methods is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus popillae, Bacillus pumilus, Bacillus siamensis, Bacillus simplex, Bacillus sphaericus, Bacillus* spp., *Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and *Streptomyces* species.

In certain embodiments of the aforementioned methods, the germinative compound is selected from the group consisting of L-alanine, L-valine, L-proline, L-leucine, L-cysteine, L-threonine, L-glutamine, L-asparagine, L-phenylalanine and analogues thereof. In some embodiments, the bacterial spore is selected from the group consisting of *B. subtilis, B. amyloliquefaciens, B. firmus, B. licheniformis, B. megaterium*, and *B. pumilus*; and the germinative compound is selected from the group consisting of L-alanine, L-valine and L-asparagine. The composition used in the aforementioned methods may further comprise a seed coating polymer. In particular embodiment, the composition comprises one or members of the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In another aspect, the present invention relates to a composition comprising a bacterial spore and a germinative compound, wherein the bacterial spore and the germinative compound are maintained in an inactive form such that the germinative compound will not induce germination of the spore until the composition is subjected to an activation environment. In some embodiments, the composition further comprises a substance which prohibits the spore and the germinative compound from interacting until the composition is subjected to the activation environment. In some embodiments, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In certain embodiments of the aforementioned composition, the bacterial spore is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus popillae, Bacillus pumilus, Bacillus siamensis, Bacillus simplex, Bacillus sphaericus, Bacillus* spp., *Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and *Streptomyces* species.

In some embodiments of the aforementioned composition, the germinative compound is selected from the group consisting of L-alanine, L-valine, L-proline, L-leucine, L-cysteine, L-threonine, L-glutamine, L-asparagine, L-phenylalanine and analogues thereof. In particular embodiments, the bacterial spore is selected from the group consisting of *B. subtilis, B. amyloliquefaciens, B. licheniformis, B. megaterium*, and *B. pumilus*; and the germinative compound is selected from the group consisting of L-alanine, L-valine and L-asparagine. In some embodiments, the composition is in the form of a dry powder. In some embodiments, the composition includes a substance which prohibits the bacterial spore and the germinative compound from interacting until the composition is subjected to an activation environment. In certain embodiments, the composition is in the form of an emulsion.

In another aspect, the present invention relates to a plant or plant part coated with a composition comprising: a) a bacterial spore; and b) a germinative compound. In another aspect, the present invention relates to a method of preparing a plant or plant part coated with a composition comprising: a) a bacterial spore; and b) a germinative compound, the method comprising treating the plant or plant part with the composition. In certain embodiments, the spore and the germinative compound are maintained in an inactive form such that the germinative compound will not induce germination of the spore until the composition is subjected to an activation environment. In certain embodiments, the composition further comprises a substance which prohibits the bacterial spore and the germinative compound from interacting until the composition is subjected to an activation environment. In certain embodiments, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent. In certain embodiments, the composition comprises an intimate mixture of the bacterial spore and the germinative compound, wherein the bacterial spore and the germinative compound are maintained in proximate position until they reach an environment conducive to germination.

In certain embodiments, the plant or plant part is selected from the group consisting of a flower, a seed, a root, a fruit, a tuber, a bulb, a rhizome, a shoot, a sprout, a seed, a leaf, a seedling, and a transplant. In certain embodiments, the plant or plant part is a seed. In certain embodiments, the plant or plant part is coated with the composition after germination or after emergence from soil. In certain embodiments, the plant or plant part is coated with the composition before germination or before emergence from soil. In certain embodiments, the plant or plant part is a plant propagative material.

In certain embodiments, the bacterial spore is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus popillae, Bacillus pumilus, Bacillus siamensis, Bacillus simplex, Bacillus sphaericus, Bacillus* spp., *Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and a species of the genus *Streptomyces*.

In certain embodiments, the germinative compound is selected from the group consisting of fructose, glucose, potassium, L-alanine, L-valine, L-proline, L-leucine, L-cysteine, L-threonine, L-glutamine, L-asparagine, L-phenylalanine, and analogues thereof. In certain embodiments, the bacterial spore is selected from the group consisting of *B. subtilis, B. amyloliquefaciens, B. firmus, B. licheniformis, B. megaterium*, and *B. pumilus*; and the germinative compound is selected from the group consisting of L-alanine, L-valine and L-asparagine.

In certain embodiments, the composition further comprises a seed coating polymer. In certain embodiments, the composition further comprises a substance selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In another aspect, the present invention relates to a method of enhancing a yield-related trait in a plant or plant part comprising treating the plant or plant part with a composition comprising a) a bacterial spore; and b) a germinative compound, wherein the yield-related trait of the plant or plant part is enhanced relative to the yield-related trait of a corresponding plant or plant part that is not coated with said composition. In certain embodiments, the spore and the germinative compound are maintained in an inactive form such that the germinative compound will not induce germination of the spore until the composition is subjected to an activation environment. In certain embodiments, the composition further comprises a substance which prohibits the bacterial spore and the germinative compound from interacting until the composition is subjected to an activation environment. In certain embodiments, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent. In certain embodiments, the composition comprises an intimate mixture of the bacterial spore and the germinative compound, wherein the bacterial spore and the germinative compound are maintained in proximate position until they reach an environment conducive to germination.

In certain embodiments of the aforementioned methods, the plant or plant part is a plant propagative material. In certain embodiments, the plant or plant part is a seed. In certain embodiments, the plant or plant part is selected from the group consisting of a flower, seed, a root, a fruit, a tuber, a bulb, a rhizome, a shoot, a sprout, a seed, a leaf, a seedling, and a transplant. In certain embodiments, the method comprises treating the plant or plant part with the composition after germination or after emergence from soil. In certain embodiments, the method comprises treating the plant or plant part with the composition before germination or before emergence from soil.

In certain embodiments, the bacterial spore is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus popillae, Bacillus pumilus, Bacillus siamensis, Bacillus simplex, Bacillus sphaericus, Bacillus spp., Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and *Streptomyces* species.

In certain embodiments, the germinative compound is selected from the group consisting of fructose, glucose, potassium, L-alanine, L-valine, L-proline, L-leucine, L-cysteine, L-threonine, L-glutamine, L-asparagine, L-phenylalanine and analogues thereof. In certain embodiments, the bacterial spore is selected from the group consisting of *B. subtilis, B. amyloliquefaciens, B. firmus, B. licheniformis, B. megaterium*, and *B. pumilus*; and the germinative compound is selected from the group consisting of L-alanine, L-valine and L-asparagine. In certain embodiments, the composition further comprises a seed coating polymer. In certain embodiments, the composition further comprises one or members of the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In another aspect, the present invention relates to a method for treating wastewater comprising adding a composition comprising a bacterial spore and a germinative compound to wastewater.

In another aspect, the present invention relates to a method for environmental remediation comprising applying a composition comprising a bacterial spore and a germinative compound to soil or water.

In another aspect, the present invention relates to a method for treating water in an aquaculture system, comprising contacting a composition comprising a bacterial spore and a germinative compound with water in an aquaculture system. In certain embodiments, the aquaculture system comprises an animal.

In another aspect, the present invention relates to a method for feeding an animal in an aquaculture system, comprising administering an animal feed comprising a composition comprising a bacterial spore and a germinative compound to the animal in the aquaculture system.

In certain embodiments of the aforementioned methods, the animal is selected from the group consisting of fish, shrimp, or mollusks. In certain embodiments, the aquaculture system comprises a pathogen selected from the group consisting of a *Vibrio* species, an *Aeromonas* species and a *Flavobacterium* species. In certain embodiments, growth of the animal is increased relative to an animal in aquaculture system that is not treated with the composition. In certain embodiments, the composition is in the form of granules, briquettes, pellets, tablets, or capsules.

In another aspect, the present invention relates to a probiotic comprising a composition comprising a bacterial spore and a germinative compound and an acceptable carrier. In certain embodiments, the acceptable carrier is selected from the group consisting of animal feed, milk, yogurt, cheese, fermented milk, cereal, fermented cereal, juice, ice-cream, or a formulation for infants or children.

In another aspect, the present invention relates to a method of preparing a probiotic, comprising mixing a composition comprising a bacterial spore and a germinative compound with an acceptable carrier. In certain embodiments, the acceptable carrier is selected from the group consisting of animal feed, milk, yogurt, cheese, fermented milk, cereal, fermented cereal, juice, ice-cream, or a formulation for infants or children.

In another aspect, the present invention relates to a method for feeding an animal comprising administering a composition comprising a bacterial spore and a germinative compound to an animal. In certain embodiments, the animal is selected from the group consisting of poultry, ruminants, calves, pigs, rabbits, horses, crustaceans, mollusks, fish and pets.

In another aspect, the present invention relates to a direct fed microbial comprising a composition comprising a bacterial spore and a germinative compound and an acceptable carrier. In certain embodiments, the carrier is selected from the group consisting of animal feed, a milk replacer, whey, vegetable oil, sucrose, silicon dioxide, polysorbate 80, propylene glycol, butylated hydroxyanisole, citric acid, ethoxyquin, limestone, rice hulls, yeast culture, malodextrin, sucrose, dextrose, dried starch and sodium silico aluminate.

In another aspect, the present invention relates to a method of preparing a direct fed microbial comprising mixing a composition comprising a bacterial spore and a germinative compound with an acceptable carrier. In certain embodiments, the carrier is selected from the group consisting of animal feed, a milk replacer, whey, vegetable oil, sucrose, silicon dioxide, polysorbate 80, propylene glycol, butylated hydroxyanisole, citric acid, ethoxyquin, limestone, rice hulls, yeast culture, malodextrin, sucrose, dextrose, dried starch and sodium silico aluminate.

In another aspect, the present invention relates to a cleaning product comprising a composition comprising a bacterial spore and a germinative compound and an acceptable carrier. In certain embodiments, the acceptable carrier is selected from the group consisting of a detergent, a soap, and a fragrance.

In another aspect, the present invention relates to a method of preparing a cleaning product comprising mixing a composition comprising a bacterial spore and a germinative compound with an acceptable carrier. In certain embodiments, the acceptable carrier is selected from the group consisting of a detergent, a soap, and a fragrance.

In another aspect, the present invention relates to a method of producing methane from waste material, comprising applying a composition comprising a bacterial spore and a germinative compound to waste material.

In another aspect, the present invention relates to a method of treating animal waste, bedding or litter comprising applying a composition comprising a bacterial spore and a germinative compound to animal waste, bedding or litter.

In another aspect, the present invention relates to a method of preparing silage comprising applying a composition comprising a bacterial spore and a germinative compound to silage.

In another aspect, the present invention relates to a method for microbial enhanced oil recovery (MEOR), comprising applying a composition comprising a bacterial spore and a germinative compound to an oil well. In certain embodiments, the bacterial spore is selected from the group consisting of *Bacillus subtilis*, *Bacillus licheniformis*, and *Bacillus mojavensis*.

In another aspect, the present invention relates to a method of treating or preventing a disease in a subject susceptible to or afflicted with the disease comprising administering to the subject an effective amount of a composition comprising a bacterial spore and a germinative compound, thereby treating or preventing the disease in the subject. In certain embodiments, the disease is a bacterial disease, a fungal disease or a viral disease. In certain embodiments, the disease is necrotic enteritis. In certain embodiments, the subject is a chicken, a turkey or a duck. In certain embodiments, the subject is infected with *Clostridium perfringens*. In certain embodiments, treating or preventing the disease results in one or more of reducing mortality, reducing lesion number, and increasing weight gain compared to a subject that is not administered the composition.

In certain embodiments of any of the aforementioned methods, the spore and the germinative compound are maintained in an inactive form such that the germinative compound will not induce germination of the spore until the composition is subjected to an activation environment.

In certain embodiments of any of the aforementioned methods, the composition further comprises a substance which prohibits the bacterial spore and the germinative compound from interacting until the composition is subjected to an activation environment. In certain embodiments of any of the aforementioned methods, the substance is selected from the group consisting of a surfactant, a sequestering agent, a plasticizer, a colorant, a dye, a brightener, an emulsifier, a flow agent, a coalescing agent, a defoaming agent, a thickener, a wax, a bactericide, a filler, a polymer, a wetting agent, and an anti-freezing agent.

In certain embodiments of any of the aforementioned methods, the composition comprises an intimate mixture of the bacterial spore and the germinative compound, wherein the bacterial spore and the germinative compound are maintained in proximate position until they reach an environment conducive to germination.

In certain embodiments of any of the aforementioned methods, the bacterial spore is selected from the group consisting of *Bacillus agri, Bacillus aizawai, Bacillus albolactis, Bacillus altitudinis, Bacillus amyloliquefaciens, Bacillus butanolivorans, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis Bacillus mycoides, Bacillus natto, Bacillus nigrificans, Bacillus popillae, Bacillus pumilus, Bacillus siamensis, Bacillus simplex, Bacillus sphaericus, Bacillus* spp., *Bacillus subtilis, Bacillus thuringiensis, Bacillus unifagellatus, Clostridium thermocellum, Clostridium ljungdahlii, Clostridium acetobutylicum, Clostridium beijerinckii, Clostridium butyricum, Pasteuria penetrans, Pasteuria thornei, Pasteuria nishizawae* and *Streptomyces* species.

In certain embodiments of any of the aforementioned methods, the germinative compound is selected from the group consisting of fructose, glucose, potassium, L-alanine, L-valine, L-proline, L-leucine, L-cysteine, L-threonine, L-glutamine, L-asparagine, L-phenylalanine and analogues thereof.

In certain embodiments of any of the aforementioned methods, the bacterial spore is selected from the group consisting of *B. subtilis, B. amyloliquefaciens, B. firmus, B. licheniformis, B. megaterium*, and *B. pumilus*; and the germinative compound is selected from the group consisting of L-alanine, L-valine and L-asparagine.

In certain embodiments of any of the aforementioned methods, the composition is in the form of a dry powder.

In certain embodiments of any of the aforementioned methods, the composition is in the form of an emulsion.

DETAILED DESCRIPTION OF THE INVENTION

In one aspect, the mixtures of the invention are comprised of a bacterial spore and a germinative compound. The bacterial species employed may be any species which forms spores, and is typically one which exhibits desirable probiotic activity in humans or animals. However, bacterial species which have other industrial applications including those useful in agriculture, environmental remediation, composting or methane production, cleaning supplies and the like may also be employed. For example, because of their ability to synthesize multiple enzymes as well as their environmental acceptability, *Bacillus* species are employed in a multitude of commercial applications. Depending upon the particular bacterial species employed, compositions of the bacteria may be suitable for agricultural, horticultural, environmental, probiotic, aquatic, industrial and sanitation uses, among others. The particular composition employed for any particular spore/germinative compound intimate mixture will depend upon the use for which such mixture is intended.

In certain embodiments, the present invention is directed to a plant or plant part coated with a composition comprising: (a) a bacterial spore; and (b) a germinative compound. The bacterial spores include species which enhance the growth of a plant, typically either by acting as a pesticide (for example, a fungicide, nematocide or insecticide); or by enhancing the environment around the propagative material for growth, (for example, by increasing the amount of nutrients available, such as nitrogen). The germinative compound aids in the rapid transformation of the bacterium from its spore to its vegetative state, thereby enabling the bacterium to more quickly enhance the growth of the plant.

Plant parts include, but are not limited to, leaves, stems, roots, flowers, buds, fruit, seeds, tubers, bulbs and rhizomes.

In certain embodiments, the plant or plant part is a plant propagative material. As is employed herein, the term "plant propagative material" is intended to include all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts, seedlings, and transplants, i.e. young plants which are to be transplanted after germination or after emergence from soil. These transplants may also be protected before transplantation by a total or partial treatment by immersion or pouring. Preferably, the plant propagative material is a seed.

Plants that are particularly useful in the present invention include monocotyledonous and dicotyledonous plants including but not limited to fodder or forage legumes, ornamental plants, food crops, trees, or shrubs selected from *Acer* spp., *Allium* spp., *Amaranthus* spp., *Ananas comosus*, *Apium graveolens*, *Arachis* spp, *Asparagus officinalis*, *Beta vulgaris*, *Brassica* spp. (e.g. *Brassica napus*, *Brassica rapa* ssp. [canola, oilseed rape, turnip rape]), *Camellia sinensis*, *Canna indica*, *Cannabis saliva*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hibiscus* spp., *Hordeum* spp. (e.g. *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g. *Lycopersicon esculenturn*, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g. *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g. *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. Especially preferred are rice, oilseed rape, canola, soybean, corn (maize), cotton, sugarcane, alfalfa, sorghum, and wheat.

The bacterium employed in the composition of this invention includes any spore-forming bacterium with industrial use, such as enhancing the growth of plants, environmental remediation, wastewater treatment, or use in aquaculture systems. For example, the enhancement of plant growth may be in the form of making additional resources available to the growing plant, such as enhancing nitrogen availability, e.g., as provided by a root colonizing bacterium (such as a rhizobacterium) or providing plant growth promoting materials such as amino acids, organic acids or hormones.

Alternatively, the bacterium may provide the plant (e.g. the plant propagative material) with protection from the harmful effects of plant pathogenic fungi or bacteria and/or soil born animals such as those belonging to the phylum Nematoda or Aschelminthes. Protection against plant parasitic nematodes and parasitic microorganisms can occur through chitinolytic, proteolytic, collagenolytic, or other activities detrimental to these soil born animals and/or detrimental to microbial populations. Bacteria exhibiting these nematicidal, fungicidal and bactericidal properties may include, but are not limited to, species including spore forming members of the phylum Firmicutes and spore forming members of the phylum Actinobacteria as listed in Bergey's Manual of Systematic Bacteriology, Second Edition (2009), hereby incorporated by reference in its entirety. Illustrative species include *Bacillus alcalophilus*, *Bacillus altitudinis*, *Bacillus alvei*, *Bacillus amyloliquefaciens*, *Bacillus aneurinolyticus*, *Bacillus anthracis*, *Bacillus aquaemaris*, *Bacillus atrophaeus*, *Bacillus boronophilus*, *Bacillus brevis*, *Bacillus caldolyyicus*, *Bacillus centrosporus*, *Bacillus cereus*, *Bacillus circulans*, *Bacillus clausii*, *Bacillus coagulans*, *Bacillus firmus*, *Bacillus flavothermus*, *Bacillus fusiformis*, *Bacillus globigii*, *Bacillus infernus*, *Bacillus larvae*, *Bacillus laterosporus*, *Bacillus lentimorbus*, *Bacillus lentus*, *Bacillus licheniformis*, *Bacillus megaterium*, *Bacillus mesentericus*, *Bacillus mojavensis*, *Bacillus mucilaginosus*, *Bacillus mycoides*, *Bacillus natto*, *Bacillus pantothenicus*, *Bacillus popilliae*, *Bacillus polymyxa*, *Bacillus pseudoanthracis*, *Bacillus pumilus*, *Bacillus schlegelii*, *Bacillus simplex*, *Bacillus sphaericus*, *Bacillus sporothermodurans*, *Bacillus stearothermophilus*, *Bacillus subtilis*, *Bacillus thermoglucosidasius*, *Bacillus thuringiensis*, *Bacillus vulgatis*, *Bacillus weihenstephanensis*, *Clostridium thermocellum*, *Clostridium ljungdahlii*, *Clostridium acetobutylicum*, *Clostridium beijerinckii*, and *Clostridium butyricum*. Preferred species include *Bacillus amyloliquefaciens*, *Bacillus brevis*, *Bacillus cereus*, *Bacillus circulans*, *Bacillus clausii*, *Bacillus coagulans*, *Bacillus firmus*, *Bacillus laterosporus*, *Bacillus lentus*, *Bacillus licheniformis*, *Bacillus megaterium*, *Bacillus polymyxa*, *Bacillus pumilus*, *Bacillus simplex*, *Bacillus sphaericus*, *Bacillus stearothermophilus*, *Bacillus subtilis*, *Bacillus thuringiensis*, *Clostridium butyricum*, *Pasteuria penetrans*, *Pasteuria thornei*, *Pasteuria nishizawae* and *Streptomyces* species.

Particularly preferred bacterial species include *B. subtilis*, *B. amyloliquefaciens*, *B. licheniformis*, *B. megaterium*, and *B. pumilus*.

The germinative compound may comprise any compound which is effective to cause germination of the particular spore-forming bacteria species employed. Typically, such germinative compounds are L-amino acids including L-alanine, L-valine, L-proline, L-leucine, L-cysteine, L-threonine, L-glutamine, L-asparagine, L-phenylalanine and analogues thereof. Such analogues can be created by one of ordinary skill in the art by making substitutions on or within groups of a base chemistry. Thus, for example, analogues of L-alanine include: L-Leu-L-Ala, L-Ala-L-Leu, L-Pro-LAla, L-Ala-L-Pro, a-L-Glu-L-Ala, L-Ala-L-Glu, L-His-L-Ala, L-Ala-L-His, L-Ala-L-Ala, Gly-L-Ala, L-Ala-Gly, N42-methylsulphonyl)ethyloxycarbonyl-L-alanine dicyclohexylammonium salt (N-MSOC-L-Ala), N-t-butoxycarbonyl-L-alanine (N-t-BOC-L-Ala), N-acetyl-L-alanine (N-Ac-L-Ala), N-2,4-dinitrophenyl-L-alanine (N-DNP-L-Ala), Ncarbobenzoxy-L-alanine (N-CBZ-L-Ala), 5-dimethyl-amino-1-naphthalenesulphonyl-L-alanine cyclohexylamine salt (N-dansyl-L-Ala), N-benzoyl-L-alanine (N-Bz-L-Ala), L-alanine methyl ester hydrochloride, L-alanine ethyl ester hydrochloride, L-alanine t-butyl ester hydrochloride, L-alanine benzyl ester hydrochloride, L-alaninamide, L-alanine p-nitroanilide hydrochloride and L-alaninol. Preferred germinative compounds include L-alanine, L-valine, and L-asparagine. Most preferably, such germinative compound is L-alanine.

Such amino acids can be employed as individual compounds, or in the form of polypeptides such as protein hydrolysates, for example casein hydrolysates. Useful polypeptides will typically comprise at least fifty percent amino acids which will function as germinants and no more than 20% amino acids which will function as inhibitors, such percentages being based upon the number of amino acids in the polypeptide.

In certain embodiments, further germinative compounds in addition to the L-amino acids may also be used to optimize germination and growth response of the bacterial spores. For example, in certain embodiments, the compositions comprise at least one L-amino acid and an additional germinative compound selected from the group consisting of fructose, glucose, and potassium ions.

Particularly preferred Bacillus/germinative compound combinations include L-alanine+Bacillus subtilis, L-alanine+Bacillus licheniformis, L-alanine+Bacillus pumilus, L-alanine+Bacillus amyloliquefaciens, L-alanine+Bacillus coagulans, L-alanine+Bacillus cereus, L-alanine+Bacillus clausii, L-alanine+Clostridium butyricum L-valine+Bacillus subtilis, L-valine+Bacillus licheniformis, L-valine+Bacillus pumilus*, L-valine+*Bacillus amyloliquefaciens*, L-valine+*Bacillus coagulans*, L-valine+*Bacillus cereus*, L-valine+*Bacillus clausii*, L-valine+*Clostridium butyricum* L-alanine+glucose+fructose+potassium ions (GFK)+*Bacillus subtilis*, L-alanine+glucose+fructose+potassium ions (GFK)+*Bacillus licheniformis*, L-alanine+glucose+fructose+potassium ions (GFK)+*Bacillus pumilus*, L-alanine+glucose+fructose+potassium ions (GFK)+*Bacillus amyloliquefaciens*, L-alanine+glucose+fructose+potassium ions (GFK)+*Bacillus coagulans*, L-alanine+glucose+fructose+potassium ions (GFK)+*Bacillus cereus*, L-alanine+glucose+fructose+potassium ions (GFK)+*Bacillus clausii*, L-alanine+glucose+fructose+potassium ions (GFK)+*Clostridium butyricum* L-asparagine+glucose+fructose+potassium ions (GFK)+*Bacillus subtilis*, L-asparagine+glucose+fructose+potassium ions (GFK)+*Bacillus licheniformis*, L-asparagine+glucose+fructose+potassium ions (GFK)+*Bacillus pumilus*, L-asparagine+glucose+fructose+potassium ions (GFK)+*Bacillus amyloliquefaciens*, L-asparagine+glucose+fructose+potassium ions (GFK)+*Bacillus coagulans*, L-asparagine+glucose+fructose+potassium ions (GFK)+*Bacillus cereus*, L-asparagine+glucose+fructose+potassium ions (GFK)+*Bacillus clausii*, L-asparagine+glucose+fructose+potassium ions (GFK)+*Clostridium butyricum* L-alanine+inosine+*Bacillus subtilis*, L-alanine+inosine+*Bacillus licheniformis*, L-alanine+inosine+*Bacillus pumilus*, L-alanine+inosine+*Bacillus amyloliquefaciens*, L-alanine+inosine+*Bacillus coagulans*, L-alanine+inosine+*Bacillus cereus*, L-alanine+inosine+*Bacillus clausii*, L-alanine+inosine+*Clostridium butyricum* L-proline+glucose+*Bacillus megaterium*, L-proline+*Bacillus megaterium*, L-lactate+*Clostridium butyricum*.

The germinative compound is present in an amount sufficient to cause the bacterial spore employed to germinate. Although this can be readily determined for any particular bacterial spore/germinative compound mixture by routine experimentation, such germinative compounds are typically formulated, prior to drying, at concentrations of from 0.0001 mg/mL to 170 mg/mL. In some embodiments, the germinative compounds are formulated, prior to drying, at concentrations of 0.0003 mg/mL to 170 mg/mL, 0.0003 mg/mL to 30 mg/mL, 0.001 mg/mL to 100 mg/mL, or 0.001 mg/mL to 10 mg/mL. In a preferred embodiment, the germinative compound is formulated, prior to drying, at concentrations of from 0.001 mg/mL to 1 mg/mL.

In order to further enhance germination, it is preferred that the spore be shocked. Spores may be shocked in a variety of standard methods, e.g., osmotic shock, heat shock, pressure shock, deprivation of nutrients, and/or exposure to certain acids. Heat shock involves heating the spores for a sufficient period of time at a temperature sufficient to induce the production of heat shock proteins. Methods of shocking bacterial spores are known in the art. For example, Atluri et al. (2006, Journal of Bacteriology 188(1): 28-36) describes one such heat shock treatment for *Bacillus subtilis.*

The compositions of this invention comprise (a) a bacterial spore and (b) a germinative compound; characterized in that such spore and germinative compound are maintained in an inactive form such that the germinative compound will not induce germination of the spore until such composition is subjected to an activation environment. Such compositions are useful for the production of the coated plant or plant part (e.g. plant propagative material) of this invention, as well as the other uses described herein such as environmental remediation, wastewater treatment, prevention or treatment of disease, oil recovery, or use in aquaculture systems.

As is employed herein, the term "activation environment" refers to an environment which permits the germinative compound and the spore to interact, such that the spore is induced to enter into a vegetative state. Such an activation environment may involve the addition of water (through rain, moisture in the soil, or water added to the coated plant propagation material prior to planting), or it may require a combination of factors such as temperature, moisture, pH or salinity.

Accordingly, such compositions may comprise dry mixtures of the spore and germinative compound; or they may include other materials (for example, low temperature melting waxes) which prohibit the spore and germinative compound from interacting until required environmental criteria have been reached. Additional materials that may be used in the composition to prevent the spore and germinative compound from interacting include, but are not limited to, surfactants, sequestering agents, plasticizers, colorants and dyes, brighteners, emulsifiers, flow agents, coalescing agents, defoaming agents, thickeners, waxes, fillers, polymers, wetting agents and anti-freezing agents. Further, such compositions may take the form of emulsions wherein the spore and germinative compound are kept from interacting due to their presence in different phases.

In certain embodiments, the spore and germinative compound are in intimate mixture with one another.

As is employed herein, the term "intimate mixture" refers to a mixture in which the spores and germinative compounds are maintained in proximate position until they reach an environment conducive to germination, i.e. an activation environment.

Such an intimate mixture can be achieved by employing processes such as spray-drying, freeze-drying, air drying or drum drying. In a preferred embodiment, the intimate mixture is produced by spray-drying or freeze-drying. When forming such intimate mixtures, it is important that the spore and germinative compound are not mixed together under conditions which would allow the germinative compound to cause the spore to germinate, as this could cause premature germination with an adverse effect upon the storage life of the mixture. This can be avoided by employing separate streams in a spray-dryer, either by using two nozzles or a single nozzle which permits the simultaneous spraying of two separate streams; or by freeze-drying under conditions (for example temperatures) which are not conducive to germination. Premature germination may also be avoided by introducing the spore mass to a solution containing the germinative compound immediately prior to drying.

In a preferred embodiment, the germinative compound is adsorbed to or absorbed by the bacterial spore in the intimate mixture. In a further embodiment, the bacterial spore and germinative compound are finely dispersed throughout the intimate mixture. In a still further embodiment, the bacterial spore and germinative compound are microscopically dispersed throughout the intimate mixture, such that individual particles consisting essentially of bacterial spores and individual particles consisting essentially of germinative compounds are not visible to the naked eye.

In one embodiment the intimate mixture is prepared by combining the bacterial spore and germinative compound in a solution prior to drying. Preferably, the bacterial spore and germinative compound are combined in a solution immediately prior to drying.

Although not wishing to be held to any theory, it is believed that the formation of an intimate mixture places the germinative compound in a proximate position where it can more preferably bind to the germination initiator sites of the spore when the mixture reaches an appropriate environment for germination. Such proximate position permits the germinative compound to outcompete germination interfering compounds (such as D-amino acids) which may be present, with the result that a higher percentage of spores will be germinated. Due to the logarithmic growth of bacteria once they enter the vegetative stage; such an increased percentage can quickly result in a several log increase in culture formation.

Such compositions may further comprise additional components, including co-germinants, nutrients, and formulation aids, provided that such additives do not induce the spore and the germinative compound to prematurely interact.

The plant or plant part (e.g the plant propagative material) to be coated according to the invention may be of any plant species that can benefit from the presence of an inoculant or a plant-growth-promoting or pesticidal microbe.

The plant or plant part (e.g. plant propagative material) may be coated with the bacterium and germinative compound by any conventional means typically employed to coat plant material (e.g. seed or other germinative material), provided that such means does not adversely affect the viability of the spores and that such means does not result in the germinative compound prematurely converting the bacterium into its vegetative state. Conventional means which may be employed include spray treatment, drip treatment, drench treatment, painting treatment, film-coat treatment, pellet-coat treatment and the like. Methods of seed coating are known in the art and are described, for example, in U.S. Pat. No. 7,989,391 and U.S. Pat. No. 5,849,320.

In certain embodiment, the plant or plant part (e.g. a seed) is coated with the composition before germination or before emergence from the growth medium in which it is planted (e.g. soil). In other embodiments, the plant or plant part is coated with the composition after germination or after emergence from the growth medium in which it is planted (e.g. soil), for example, by spraying the composition onto a plant growing in a field or greenhouse.

When applying such coating, it is important that the spore and germinative compound are not mixed together under conditions which would allow the germinative compound to cause the spore to germinate, as this could cause premature germination with an adverse effect upon the storage life of the mixture. One way in which this can be avoided is by employing separate streams in a spray-dryer, either by using two nozzles or a single nozzle which permits the simultaneous spraying of two separate streams; or by freeze-drying under conditions (for example temperatures) which are not conducive to germination.

In addition to biologically active ingredients, seed coating compositions may include many materials and additives that are either part of the formulations of the active ingredient or contribute to the handling qualities of the seed coating or its functionality and durability on the seed. An example of a coating additive is a coating polymer which binds the active ingredients to the seed. Seed-coating polymers may include, for example, but are not limited to, proteins, polysaccharides, polyesters, polyurethanes, polymers prepared from unsaturated monomers, and combinations thereof.

Other additives contributing to the handling qualities of the seed coating or its functionality and durability on the seed include but are not limited to surfactants, sequestering agents, plasticizers, colorants and dyes, brighteners, emulsifiers, flow agents, coalescing agents, defoaming agents, thickeners, waxes, bactericides, fillers, polymers, wetting agents and anti-freezing agents. The nature and action of such additives are well-known to those skilled in the art of formulation. Additives should not interfere with the action of the bacterium.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of binder in the coating can vary, but will be in the range of about 0.01 to about 25% of the weight of the seed, more preferably from about 0.05 to about 15%, and even more preferably from about 0.1% to about 10%.

The propagative material coating may optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids, which may be used, include calcium bentonite, kaolin, china clay, talc, perlite, mica, vermiculite, silicas, quartz powder, montmorillonite and mixtures thereof. Sugars, which may be useful, include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from about 0.1 to about 20% by weight.

The treated seeds may also be enveloped with a film overcoating to protect the active components coating. Such overcoatings are known in the art and may be applied using conventional fluidized bed and drum film coating techniques.

The invention also relates to a method of enhancing a yield-related trait of a plant or plant part (e.g. a plant propagative material) comprising coating the plant with a composition comprising: a) a bacterial spore; and b) a germinative compound, wherein the yield-related trait of the plant is enhanced relative to the yield-related trait of a corresponding plant that is not coated with said composition.

As used herein, the term "yield-related trait" refers to any trait that may contribute to the increased yield of a plant. The yield-related traits that may be enhanced by the methods of the present invention include, but are not limited to, total seed germination, rate of seed germination (e.g. the number of days required for seed germination), plant biomass, disease tolerance, insect tolerance, drought tolerance, heat tolerance, cold tolerance, salinity tolerance, tolerance to heavy metals, total yield, seed yield, flowering time (e.g. early flowering time), root growth, early vigor, plant biomass, plant size, total plant dry weight, above-ground dry weight, above-ground fresh weight, leaf area, stem volume, plant height, rosette diameter, leaf length, root length, root mass, tiller number, and leaf number.

In particular embodiments, the yield-related trait is selected from the group consisting of total yield, total seed germination, rate of seed germination, plant biomass, insect tolerance, early flowering time, and drought tolerance.

As used herein, the term "total seed germination" refers to the percentage of seeds which germinate after planting.

As used herein, the term "biomass" refers to the total weight of a plant. Within the definition of biomass, a distinction may be made between the biomass of one or more parts of a plant, which may include any one or more of the following: aboveground parts including, but not limited to, shoot biomass, seed biomass, leaf biomass; aboveground harvestable parts including, but not limited to, shoot biomass, seed biomass, leaf biomass; parts below ground, including, but not limited to, root biomass, tubers, bulbs; harvestable parts below ground, including, but not limited to, root biomass, tubers, bulbs; harvestable parts partially below ground including, but not limited to, beets and other hypocotyl areas of a plant, rhizomes, stolons or creeping rootstalks; vegetative biomass including, but not limited to, root biomass, shoot biomass; reproductive organs; and propagules including, but not limited to, seeds.

As used herein, the term "early flowering time" refers to a plant which begins to flower earlier than a control plant. Thus, this term refers to plants that show an earlier start of flowering. Flowering time of plants can be assessed by counting the number of days ("time to flower") between sowing and the emergence of a first inflorescence. The "flowering time" of a plant can for instance be determined using the method as described in WO07/093444, the entire contents of which are incorporated herein by reference.

As used herein, the term "drought conditions" refers to any stress which leads to a lack of water content in plants, a lack of water availability to plants, a lack of water uptake potential in plants, or a reduction in the water supply to plants. Specifically, a "drought" refers to a deficiency of precipitation resulting from a short term or long-term weather pattern. Drought conditions are determined easily by one of ordinary skill in the art. For example, the Palmer Drought Severity Index (PDSI), which is a measure of soil moisture, the Crop Moisture Index (CMI), and the Z index can be used to determine drought conditions.

Yield-related traits may be enhanced using the methods of the present invention. For example, in some embodiments, any of the yield-related traits described herein may be increased by at least about 5, 10, 15, 20, 25, 30, 35, 40, 45, 50, 55, 60, 65, 70, 75, 80, 85, 90, 95, 100, 150, 200, 300, 400, 500, 600, 700, 800, 900 or 1000% in a plant (e.g. a plant propagative material) to which a composition of the invention has been applied relative to a control plant propagative material to which a composition of the invention has not been applied.

For example, in some embodiments, total seed germination may be increased by at least about 1, 2, 3, 4, 5, 10, 15, 20, 25, 30, 35, 40, 45, 50, 55, 60, 65, 70, 75, 80, 85, 90, 95, or 100% in a plant propagative material (e.g. a seed) to which a composition of the invention has been applied relative to a control plant propagative material (e.g. a seed) to which a composition of the invention has not been applied. Any of these values may be used to define a range for the increase in total seed germination. For example, in some embodiments, seed germination may be increased by 5-10%, 5-20%, or 5-50%. In another embodiment, the number of days required for seed germination may be decreased by 1 day in a plant propagative material (e.g. a seed) to which a composition of the invention has been applied, as compared to a control plant propagative material (e.g. a seed) to which a composition of the invention has not been applied. In one embodiment, the days required for seed germination may be decreased by 0.5 days, 1 day, 1.5 days, 2 days, 3 days, 4 days, 5 days, 6 days, 7 days, 8 days, 9 days, 10 days or 14 days in a plant propagative material (e.g. a seed) to which a composition of the invention water has been applied, as compared to a control plant propagative material (e.g. a seed) to which a composition of the invention has not been applied. Any of these values may be used to define a range for the decrease in the number of days required for seed germination. For example, the days required for seed germination may be decreased by 1-2 days, 1-5 days, or 2-5 days.

In another embodiment, plant biomass may be enhanced by at least about 1, 2, 3, 4, 5, 10, 15, 20, 25, 30, 35, 40, 45, 50, 55, 60, 65, 70, 75, 80, 85, 90, 95, or 100% in a plant (e.g. a plant propagative material) to which a composition of the invention has been applied, as compared to a control plant (e.g. a plant propagative material) to which a composition of the invention has not been applied. Any of these values may be used to define a range for the increase in plant biomass. For example, in some embodiments, plant biomass is increased by 5-10%, 5-20%, or 5-50%.

In some embodiments, insect tolerance may be enhanced by at least about 1, 2, 3, 4, 5, 10, 15, 20, 25, 30, 35, 40, 45, 50, 55, 60, 65, 70, 75, 80, 85, 90, 95, or 100% in a plant (e.g a plant propagative material) to which a composition of the invention has been applied, as compared to a control plant (e.g. a plant propagative material) to which a composition of the invention has not been applied. For example, in some embodiments, insect tolerance is increased by 5-10%, 5-20% or 5-30%.

Insect tolerance, disease tolerance and environmental stress tolerance (e.g., drought tolerance) may be measured by measuring any of the yield related traits described herein under biotic or abiotic stress conditions. For example, drought tolerance may be determined by measuring percent germination, rate of germination, plant biomass, yield, or seed yield under drought conditions. The insect tolerance, disease tolerance, or environmental stress tolerance may be quantified by measuring the yield-related trait under the appropriate conditions. For example, a plant (e.g a plant propagative material) treated with a composition of the invention that exhibited a 10% increase in yield relative to a plant propagative material that was not treated with the composition would be determined to exhibit a 10% increase in drought tolerance. As another example, a plant (e.g. a plant propagative material) treated with a composition of the invention that exhibited a 10% increase in the rate of leaf out, as compared to a plant (e.g. a plant propagative material) that was not treated with the composition would be determined to exhibit a 10% increase in insect tolerance. A plant with increased rate of leaf out is more resistant to insect infestation or attack.

In some embodiments, disease tolerance or herbivore tolerance may be increased by at least about 1, 2, 3, 4, 5, 10, 15, 20, 25, 30, 35, 40, 45, 50, 55, 60, 65, 70, 75, 80, 85, 90, 95, or 100% in a plant (e.g a plant propagative material) to which a composition of the invention has been applied relative to a control plant (e.g a plant propagative material) to which a composition of the invention has not been applied. In some embodiments, drought tolerance may be increased by at least about 1, 2, 3, 4, 5, 10, 15, 20, 25, 30, 35, 40, 45, 50, 55, 60, 65, 70, 75, 80, 85, 90, 95, or 100% in a plant (e.g a plant propagative material) to which a composition of the invention has been applied relative to a control plant (e.g a plant propagative material) to which a composition of the invention has not been applied. Any of these values may be used to define a range for the increase in disease tolerance or herbivore tolerance. For example, in some embodiments, the increase in disease tolerance or herbivore tolerance is 5-10%, 5-20%, or 5-30%.

In some embodiments, heat tolerance or cold tolerance may be increased by at least about 1, 2, 3, 4, 5, 10, 15, 20, 25, 30, 35, 40, 45, 50, 55, 60, 65, 70, 75, 80, 85, 90, 95, or 100% in a plant (e.g a plant propagative material) to which a composition of the invention has been applied relative to a control plant (e.g a plant propagative material) to which a composition of the invention has not been applied. Any of these values may be used to define a range for the increase in heat tolerance of cold tolerance. For example, in some embodiments, the increase in heat tolerance or cold tolerance is 5-10%, 5-20% or 5-30%.

In some embodiments, salinity tolerance or tolerance to heavy metals may be increased by at least about 1, 2, 3, 4, 5, 10, 15, 20, 25, 30, 35, 40, 45, 50, 55, 60, 65, 70, 75, 80, 85, 90, 95, or 100% in a plant (e.g. a plant propagative material) to which a composition of the invention has been applied relative to a control plant (e.g a plant propagative material) to which a composition of the invention has not been applied. Salinity tolerance or tolerance to heavy metals may be determined using standard methods in the art. For example, salinity may be determined by measuring the exchange of cations, e.g., calcic to sodic. Any of these values may be used to define a range for the increase is salinity tolerance or tolerance to heavy metals. For example, in some embodiments, the increase in salinity tolerance or tolerance to heavy metals may be 5-10%, 5-20% or 5-30%.

In some embodiments, total yield may be increased by at least about 1, 2, 3, 4, 5, 10, 15, 20, 25, 30, 35, 40, 45, 50, 55, 60, 65, 70, 75, 80, 85, 90, 95, or 100% in a plant (e.g a plant propagative material) to which a composition of the invention has been applied relative to a control plant (e.g a plant propagative material) to which a composition of the invention has not been applied. Any of these values may be used to define a range for the increase in total yield. For example, in some embodiments, total yield is increased by 1-5%, 1-10%, or 1-15%.

In some embodiments, root growth, early vigor, plant size, total plant dry weight, above-ground dry weight, above-ground fresh weight, leaf area, stem volume, plant height, rosette diameter, leaf length, root length, root mass, tiller number, or leaf number may be increased by at least about 1, 2, 3, 4, 5, 10, 15, 20, 25, 30, 35, 40, 45, 50, 55, 60, 65, 70, 75, 80, 85, 90, 95, or 100% in a plant (e.g. a plant propagative material) to which a composition of the invention has been applied relative to a control plant (e.g. a plant propagative material) to which a composition of the invention has not been applied. Any of these values may be used to define a range for the increase in root growth, early vigor, plant size, total plant dry weight, above-ground dry weight, above-ground fresh weight, leaf area, stem volume, plant height, rosette diameter, leaf length, root length, root mass, tiller number, or leaf number. For example in some embodiments, root growth, early vigor, plant size, total plant dry weight, above-ground dry weight, above-ground fresh weight, leaf area, stem volume, plant height, rosette diameter, leaf length, root length, root mass, tiller number, or leaf number may be increased by 1-5%, 5-10%, or 5-20%.

Generally, an "enhanced yield-related trait" or an "increase in a yield-related trait" refers to a level of the trait in a test plant (e.g a plant propagative material) that is greater than the standard error of the assay employed to assess the level of the trait, and is preferably at least twice, and more preferably three, four, five or ten times the level of the trait in a control sample (e.g., sample of a plant propagative material that has not been contacted with a composition of the invention) and preferably, the average expression level of the trait in several control samples.

Values and ranges included and/or intermediate within the ranges set forth herein are also intended to be within the scope of the present disclosure. Ranges having values recited herein as an upper or lower limit are also intended to be within the scope of the present disclosure.

The invention also provides a method for treating wastewater comprising adding a composition comprising a bacterial spore and a germinative compound as described herein to wastewater. The compositions may be used for the treatment of any wastewater including municipal, industrial or agricultural wastewater, lift stations, pulp and paper wastewater, food processing wastewater, petrochemical wastewater and animal waste wastewater. The compositions may also be used for onsite wastewater treatment in septic tanks, grease traps and holding tanks. In certain embodiments, the compositions may be used to degrade fats, oils and grease in waste water generated by restaurants and commercial kitchens. The compositions may also be added to small-scale wastewater holding tanks for breaking down waste in boats, portable toilets and other small waste holding systems.

The wastewater treatment methods of the invention may also be conducted in a variety of reactor systems. For example, while the wastewater treatment will typically be conducted in a tank, the reaction may be conducted in any vessel or reservoir used for wastewater storage provided that suitable conditions are provided to maintain a suitable environment to support the growth and biological activity of the bacteria in the composition. Suitable wastewater treatment reactor systems include but are not limited to suspended-growth bioreactors and attached-growth bioreactors. In suspended-growth bioreactors, the composition may be mixed with the wastewater by the agitation of the liquid. In an attached-growth bioreactor, various solid support media are provided to allow the bacteria in the composition to attach to the surface thereof. Suitable media include, but are not limited to trickling filters, rotating biological contactors, packed-bed reactors, and others known in the art. Yet another attached-growth bioreactor that is suitable for use herein is a fluidized or moving bed reactor. In this system, bio-carriers containing the bacteria remain suspended in the wastewater being treated, fluidized by the drag forces associated with the mixing of the water. The bacteria may be entrapped in polymeric porous materials such as particles of polyvinyl alcohol (PVA), polyethylene glycol (PEG), or other polymer gels such as calcium alginate. The bacteria may be attached forming biofilms in suspended carriers such as K1, K3, MiniChip, and BiofilmChip plastic carriers (AnoxKaldnes, Sweden). Fluidized bed reactors allow the populations of microorganisms to increase rapidly, thus reducing the time necessary for wastewater treatment. Methods of wastewater treatment using bacterial strains are known in the art and are described, for example, in U.S. Patent Application Publication Nos. 2012/0000849 and 2011/0180476.

In certain embodiments the compositions used for wastewater treatment comprises a bacterial spore selected from the group consisting of *Bacillus megaterium, Bacillus amyloliquefaciens, Bacillus licheniformis, Bacillus subtilis*, and *Bacillus pumilus*.

The invention also provides methods of environmental remediation comprising applying any of the aforementioned compositions comprising a bacterial spore and a germinative compound to soil or water. *Bacillus* species may be used for environmental remediation both in water and land. The mode of action for soil remediation is much the same as described above for wastewater treatment. The bacteria break down chemicals and pollutants via enzyme and acid generation that further break down the pollutant or bind it in a more non-reactive form.

The compositions described herein may be used in bioremediation and biologically mediated chemical reduction of environmental media and wastes contaminated with a broad range of contaminants including halogenated organic compounds (e.g., trichloroethene, tetrachloroethene, freon) and inorganic contaminants such as arsenic-based pesticides, cyanides, chromium (VI), uranium (VI) and the oxidized forms of other toxic metals. The compositions may also be used for the treatment of other hydrophobic, and therefore recalcitrant, organic contaminants, such as organochlorine pesticides, polychlorinated biphenyls (PCBs) and polycyclic aromatic hydrocarbons (PAHs), by promoting processes which increase the bioavailability and biogeochemical reactivity of these contaminants. Bioremediation processes which may be enhanced by the compositions include the biodegradation and biologically mediated chemical reduction of organic contaminants, such as halogenated solvents, organochlorine pesticides and chlorinated hydrocarbons, which are converted by the bacteria into non-hazardous mineral forms and/or less hazardous by-products. In addition, the compositions may promote the biologically mediated chemical reduction of inorganic contaminants, such as arsenic-based pesticides, cyanides, chromium (VI), uranium (VI) and the oxidized forms of other toxic metals.

In certain embodiments, the compositions may be prepared in the forms of granules, briquettes, pellets, tablets, or capsules. The compositions may be applied to and optionally mixed into the contaminated wastes (e.g., sludges, solid and/or liquid wastes, and the like) or other contaminated media such as soils, sediments, or water bodies, and the like. For applications involving the treatment of contaminated ground waters and aquifer media, the compositions (e.g., granules) may be applied in filter socks, canisters, or cartridges within wells installed in the contaminated areas.

In another aspect, the invention relates to methods of methane production from waste material comprising applying a composition comprising a bacterial spore and germinative compound as described herein to waste material. In certain embodiments, the waste material is from a municipal waste site. The breakdown of waste material by the bacteria may encourage the communal activity of other bacteria that produce methane for capture as an energy source.

Methane may be produced from waste material comprising organic matter in the form of a slurry or sludge, for example, sludge from wastewater treatment, treatment of sludge produced in water purification, or treatment of particulate biodegradable organic waste. In certain embodiments, the waste material is a wastewater treatment biosolid. Methods of producing methane may involve the treatment of complex organic material, both the liquid and residual solids fractions, using thermal hydrolysis. Anaerobic digestion by bacteria may then be used for production of methane. Production of methane from waste material is described in the art, for example in U.S. Pat. No. 8,470,567, U.S. Pat. No. 7,311,834, U.S. Pat. No. 7,101,482, U.S. Pat. No. 6,966,989, and U.S. Pat. No. 7,332,095.

The invention also provides methods for treating water in an aquaculture system, comprising contacting any of the aforementioned compositions comprising a bacterial spore and a germinative compound with water in an aquaculture system. The compositions may be added directly to the water, or may be used in a biofilter system as described, for example, in U.S. Pat. No. 7,082,893. The compositions may be used in an aquaculture system to remediate and break down the waste generated by aquatic species raised for food such as shrimp, fish or mollusks (e.g. clams). In a particular embodiment, the aquaculture system is a hatchery. The compositions may also be utilized in aquaculture to cycle nutrients, break down lipids, proteins, starches as well as produce amino acids & enzymes which enhance feed conversion. The compositions may also be used to generate natural antibiotics and provide competitive exclusion to protect against pathogens in the environment as well as the animal's gastrointestinal tract. In a particular embodiment, the pathogen in the aquaculture system is a *Vibrio* species, for example, *Vibrio chagasii* or *Vibrio coralliilyticus*. In certain embodiments, the pathogen in the aquaculture system is one of the pathogens listed in Table 1A below. This generation of natural antibiotics and competitive exclusion against pathogens may also be utilized in human probiotics or direct fed microbials for production animals and companion animals.

In certain embodiments, the composition is added to the aquaculture system by suspending the composition in water and then adding the suspension immediately to the tank after the daily water change. In certain embodiments, the composition is added to the aquaculture system at a rate for $1\times10^3$, $1\times10^4$, $1\times10^5$, $1\times10^6$, $1\times10^7$, $1\times10^8$ or $1\times10^9$ cfu of the bacteria per ml of water in the aquaculture system. Any of these values may be used to define a range for the concentration of the bacteria of the composition in the aquaculture system. For example, the concentration of the bacteria may be $1\times10^5$-$1\times10^6$ or $1\times10^4$-$1\times10^6$ cfu/ml of water.

Treating the water in an aquaculture system infected with a pathogen with a composition described herein may increase the percent survival of animals in the aquaculture system relative to animals in an infected aquaculture system that is not treated with the composition. In some embodiments, treatment of the water in the aquaculture system increases percent survival of the animals by at least about 1, 2, 3, 4, 5, 10, 15, 20, 25, 30, 35, 40, 45, 50, 55, 60, 65, 70, 75, 80, 85, 90, 95, 100, 200, 300, 400, or 500% relative to animals in an infected aquaculture system that is not treated with the composition. In a particular embodiment, percent survival is increased by at least 400%.

The invention also relates to a method for feeding an animal in an aquaculture system, comprising administering an animal feed comprising any of the aforementioned compositions comprising a bacterial spore and a germinative compound to the animal in the aquaculture system. In certain embodiments, the animal is selected from the group consisting of fish, shrimp, or mollusks. In certain embodiments, the growth (e.g. body weight) of the animal in the aquaculture system is increased relative to a control animal that is administered an animal feed that does not comprise the composition. In certain embodiments, the animal is infected with at least one of the pathogens provided in Table 1A below.

For example, in some embodiments, body weight may be increased by at least about 1, 2, 3, 4, 5, 10, 15, 20, 25, 30, 35, 40, 45, 50, 55, 60, 65, 70, 75, 80, 85, 90, 95, or 100% in an animal to which an animal feed comprising a composition of the invention has been administered relative to a control animal to which an animal feed comprising a composition of the invention has not been administered. Any of these values may be used to define a range for the increase in body weight. For example, in some embodiments, body weight may be increased by 5-10%, 5-20%, or 5-50%.

In certain embodiments of the aforementioned methods, the bacterial spore is selected from the group consisting of *Bacillus licheniformis, Bacillus subtilis* and *Bacillus pumilis*.

The invention also provides bacterial spore germinative compound mixtures for use in foods for human consumption or for animal feed. In certain embodiments, the food for human consumption is a probiotic. In certain embodiments, the animal feed is a direct fed microbial. As used herein the term "probiotic" refers to a food product for human consumption that contains viable microorganisms, i.e. microorganisms that are capable of reproducing, such as bacterial spores. As used here in the term "direct fed microbial" refers to a feedstuff for consumption by animals (i.e. animal feed) that contains viable microorganisms, i.e. microorganisms that are capable of reproducing, such as bacterial spores. See, for example, U.S. Pat. No. 8,420,074. The probiotic or direct fed microbial may comprise any of the compositions comprising a bacterial spore and germinative compound as described herein. The use of spore forming bacteria including certain *Bacillus* strains as probiotics for both humans and animals has become prevalent in recent years. As is noted in Knap et al. (WO 2010/070005) species such as *Bacillus subtilis* and *Bacillus licheniformis* are used as supplements in animal feed in order to promote growth by increasing the digestion and availability of nutrients from animal feed. *Bacillus coagulans* is an active ingredient in commercial probiotic products for human consumption, helping to aid in the digestion of proteins, lactose and fructose.

In certain embodiments, the food or animal feed comprises a bacterial spore selected from the group consisting of *Bacillus pumilis, Bacillus lentus, Bacillus subtilis, Bacillus licheniformis*, and *Bacillus coagulans*.

The beneficial effects of direct fed microbials comprising bacteria include competitive exclusion of pathogens, the breaking down of feed by bacterial enzymes and acids for more efficient conversion, stimulation of the immune system, and production of antibiotics and bacteriocins by the bacteria. The bacterial spores and, after germination of the spores, bacteria in their vegetative state also improve the environment for the animal by reducing ammonia odors and breaking down manure for easier handling.

An acceptable carrier may be added to the direct fed microbial. The acceptable carrier may be a liquid carrier, a solid carrier, a water soluble carrier, or any other suitable carrier. A preferred liquid carrier is a milk replacer. Milk replacers are typically milk substitutes in powdered form that are mixed with water to form a composition that resembles milk. Another preferred liquid carrier is water. Dry carriers include, but are not limited to, animal feed, whey, limestone (calcium carbonate), rice hulls, yeast culture, dried starch, and sodium silico aluminate. In certain embodiments, the water soluble carrier is selected from the group consisting of whey, maltodextrin, sucrose, dextrose, dried starch, and sodium silico aluminate. In other embodiments, the acceptable carrier for a direct fed microbial is selected from the group consisting of vegetable oil, sucrose, silicon dioxide, polysorbate 80, propylene glycol, butylated hydroxyanisole, citric acid, and ethoxyquin.

In certain embodiments, the direct fed microbial comprises a bacterial spore selected from the group consisting of *Bacillus subtilis, Bacillus licheniformis*, and *Bacillus coagulans*. In other embodiments the direct fed microbial comprises a bacterial spore selected from the group consisting of *Bacillus megaterium, Bacillus amyloliquefaciens, Bacillus licheniformis, Bacillus subtilis*, and *Bacillus pumilus*.

In certain embodiments, the direct fed microbial is fed as a milk supplement (replacer) fed during lactation 7-19 days prior to weaning, a single dose of a gel paste or drench given 1-2 days prior to weaning followed by dosing in water systems in the nursery for 7 days, or a single dose of a gel paste or drench given 1-2 days prior to weaning followed by dosing in gruel feed in the nursery for 2-3 days. The direct fed microbial can be fed in other forms, for differing periods of time, and at different stages of animal growth.

In certain embodiments, the animal is fed the direct fed microbial such that the amount of the bacterial strain delivered to the animal is at least $1\times10^7$ colony forming units (CFU), $1\times10^8$ CFU, $1\times10^9$ CFU or $1\times10^{10}$ CFU per day. However, it should be noted that higher and lower doses of the bacterial strain may be fed to the animal.

In certain embodiments, the animal feed (e.g. a probiotic or direct microbial) comprises at least about $1\times10^3$, $1\times10^4$, $1\times10^5$, $1\times10^6$, $1\times10^7$, $1\times10^8$ or $1\times10^9$ CFU of the bacterial strain to be delivered to the animal per gram of animal feed.

Any of these values may be used to define a range for the concentration of the bacterial strain in the animal feed. For example, in some embodiments, the animal feed comprises at least about $1\times10^5$-$1\times10^7$ CFU, $5\times10^5$-$5\times10^6$ CFU, or $1\times10^6$-$5\times10^6$ CFU of the bacterial strain per gram of animal feed.

In certain embodiments, the food for human consumption (e.g. a probiotic) comprises at least about $1\times10^3$, $1\times10^4$, $1\times10^5$, $1\times10^6$, $1\times10^7$, $1\times10^8$ or $1\times10^9$ CFU of the bacterial strain to be delivered to the human per gram of food for human consumption. Any of these values may be used to define a range for the concentration of the bacterial strain in the food for human consumption. For example, in some embodiments, the food for human consumption comprises at least about $1\times10^5$-$1\times10^7$ CFU, $5\times10^5$-$5\times10^6$ CFU, or $1\times10^6$-$5\times10^6$ CFU of the bacterial strain per gram of animal feed.

In another aspect, the invention also relates to methods of preparing a direct fed microbial comprising mixing a composition comprising a bacterial spore and germinative compound as described herein with an acceptable carrier for a direct fed microbial as described above.

In another aspect the invention relates to a method for feeding an animal comprising administering a composition comprising a bacterial spore and germinative compound as described herein to an animal. In certain embodiments, the animal feed may be administered to the animal in conjunction with other animal feed ingredients. The animal may be any animal of interest. In certain embodiments, the animal is an animal selected from the group consisting of poultry, ruminants, calves, pigs, rabbits, horses, fish and pets. The compositions may be administered at a dose of at least $10^3$, $10^4$, $10^5$, $10^6$, $10^7$, $10^8$ or $10^9$ colony forming units (CFU) of bacteria per gram of feed. The compositions may also be administered to the animal by adding the composition to drinking water for the animal, spraying the composition onto the animals, or application via paste, gel or bolus.

In certain embodiments, the probiotic comprises a composition comprising a bacterial spore and a germinative compound as described herein and an acceptable carrier. In certain embodiments, the acceptable carrier for the probiotic is selected from the group consisting of milk, yogurt, cheese, fermented milk, cereal, fermented cereal, juice, ice-cream, or a formulation for infants or children. The invention also relates to a method of preparing a probiotic, comprising mixing a composition comprising a bacterial spore and a germinative compound as described herein with an acceptable carrier for the probiotic as described above.

In another aspect, the invention relates to methods of treating soil, growing medium, or compost comprising applying to the soil, growing medium, or compost a composition comprising a bacterial spore and a germinative compound as described herein. The bacterial spores may be mixed with any suitable carrier and sprayed or spread over the soil, growing medium, or compost. Upon germinating and entering the vegetative state, the bacterial spores begin to utilize the surrounding medium and subsequently produce beneficial materials for plants via nutrient cycling (breaking down materials to simpler forms that can be taken up by the plant) or releasing bound materials. Materials made available by nutrient cycling include Nitrogen, Phosphorus, Potassium, Zinc, Iron, Manganese, and other micronutrients. The bacteria also produce antibiotics, anti-fungal compounds, bacteriocins, organic acids, amino acids, enzymes and siderophores that can be utilized by the plant or work in conjunction with the surrounding rhizosphere to provide benefit to the plant.

In another aspect, the invention relates to a method of increasing pathogen or insect resistance in a plant comprising applying to the plant a composition comprising a bacterial spore and a germinative compound as described herein, wherein the pathogen or insect resistance is increased relative to a corresponding plant that has not been treated with the composition. Bacteria may increase pathogen or insect resistance in a plant by inducing resistance, for example, Induced Systemic Resistance (ISR) to pathogens and insects. Bacteria may also increase pathogen resistance in a plant by forming a biofilm and excluding the growth of other bacteria or fungi through competitive exclusion for nutrients and space.

In certain embodiments, the pathogen is a fungal pathogen, a bacterial pathogen or a viral pathogen. In certain embodiments the composition used for increasing resistance to a fungal pathogen comprises a bacterial spore selected from the group consisting of *Bacillus megaterium, Bacillus amyloliquefaciens, Bacillus licheniformis, Bacillus subtilis*, and *Bacillus pumilus*.

In another aspect, the invention relates to a cleaning product comprising a composition comprising a bacterial spore and a germinative compound as described herein and an acceptable carrier. In certain embodiments, the cleaning product comprises a bacterial spore selected from the group consisting of *Bacillus megaterium, Bacillus amyloliquefaciens, Bacillus licheniformis, Bacillus subtilis*, and *Bacillus pumilus*. In certain embodiments, the acceptable carrier for the cleaning product is selected from the group consisting of a detergent, a soap, and a fragrance. In certain embodiments, the cleaning compounds is for use in bathrooms and transit areas. One of the ways that bacteria may improve the effectiveness of a cleaning product is by using urea as an energy source, thereby breaking down the urea and reducing odors such as ammonia. Once the bacterial spores have germinated, the vegetative state of the bacteria can grow in the grout between tiles and in the padding of carpets to provide breakdown of unwanted materials.

In certain embodiments, the cleaning product comprises at least about $1\times10^3$, $1\times10^4$, $1\times10^5$, $1\times10^6$, $1\times10^7$, $1\times10^8$ or $1\times10^9$ CFU of the bacterial spores per gram of the cleaning product. Any of these values may be used to define a range for the amount of the bacterial spore in the cleaning product. For example, in some embodiments, the cleaning product comprises at least about $1\times10^5$-$1\times10^7$ CFU, $5\times10^5$-$5\times10^6$ CFU, or $1\times10^6$-$5\times10^6$ CFU of the bacterial strain per gram of the cleaning product.

The invention also relates to a method of preparing a cleaning product comprising mixing a composition comprising a bacterial spore and a germinative compound as described herein with an acceptable carrier. In certain embodiments, the acceptable carrier used in the method is selected from the group consisting of a detergent, a soap, and a fragrance.

The invention also relates to a method of treating animal waste, bedding or litter comprising applying a composition comprising a bacterial spore and a germinative compound as described herein to animal waste, bedding or litter.

In another aspect, the invention relates to silage comprising a composition comprising a bacterial spore and a germinative compound as described herein. The invention also relates to a method of preparing silage comprising applying a composition comprising a bacterial spore and a germinative compound to silage. Silage is a type of animal feed produced by fermenting plant biomass such as grass, hay, cereal crops or maize in silos or other closed containers.

When treating agricultural raw materials for the production of silage, the plant biomass, such as grass or maize is mixed with lactic acid bacteria to form ensilage. Production of silage is a well-known method for increasing the stability of animal feed and to improve the properties of the raw materials. For the production of silages, maize and grasses, millet, cereals with or without grains and leguminous plants are suitable as raw materials. To produce silages, silaging aids, so-called silage starters, are frequently used, comprising both chemical additives and microbial additives. Microbial additives may also be added to silage, for example, to inhibit the growth of contaminative organisms, to reduce mycotoxins, or to reduce methane emissions of ruminants. Methods for preparing silage containing microbial additives are known in the art and are described, for example, in US 2011/0142991.

In certain embodiments, the silage comprises at least about $1\times10^3$, $1\times10^4$, $1\times10^5$, $1\times10^6$, $1\times10^7$, $1\times10^8$ or $1\times10^9$ CFU of the bacteria per gram of silage. Any of these values may be used to define a range for the concentration of the bacterial strain in the silage. For example, in some embodiments, the silage comprises at least about $1\times10^5$-$1\times10^7$ CFU, $5\times10^5$-$5\times10^6$ CFU, or $1\times10^6$-$5\times10^6$ CFU of the bacterial strain per gram of silage.

The invention also relates to a method for microbial enhanced oil recovery (MEOR), comprising applying a composition comprising a bacterial spore and a germinative compound to an oil well. In certain embodiments, the composition is applied to the bore hole of the oil well or to a reservoir of the oil well. MEOR is a tertiary oil recovery process where microorganisms are used for the mobilization of crude oil trapped in mature oil formations. MEOR may improve oil recovery by altering oil, water or rock interfacial properties or through changes in flow behavior due to bioclogging. Methods for MEOR are described, for example, in U.S. Pat. Nos. 8,746,334 and 8,826,975 and Al-Sulaimani et al., 2011, Biotechnol. Bioinf. Bioeng. 1(2): 147-158. MEOR may be used to enhance oil recovery by re-pressurizing a drainage portion of the oil well to a target pressure or by generating a target amount of gas by a gas producing bacterial strain. The composition comprising the bacterial spores and germinative compound may be injected through the oil well into the reservoir of the oil well. The well may then be sealed until the pressure in the well reaches a target pressure or a target amount of gas is generated to increase oil production from the well.

Underground oil reservoirs are frequently flooded with water after the reservoirs have become significantly depleted in order to supply additional pressure to assist oil recovery. In some embodiments, the compositions described herein are injected into a well with this flood water. The flood water in this instance acts as an aqueous liquid carrier. Alternatively, the compositions of the invention can be injected into a well separately from the flood water. In this later case, another aqueous liquid, that is, a liquid other than the flood water, is provided to serve as a carrier. Methods of injecting microorganisms into oil wells through flood water are described, for example, in U.S. Pat. No. 5,044,435.

In certain embodiments, Bacillus or Clostridium species may be used for MEOR. In a particular embodiment, the bacterial species used for MEOR are selected from the group consisting of Bacillus subtilis, Bacillus licheniformis and Bacillus mojavensis.

The invention also relates to a method of treating or preventing a disease in a subject comprising administering to the subject an effective amount of a composition comprising a bacterial spore and a germinative compound as described herein, thereby treating or preventing the disease in the subject. An "effective amount" is that amount sufficient to treat a disease in a subject. An effective amount can be administered in one or more administrations. In certain embodiments, the composition is administered to the subject by adding the composition to feed, for example, animal feed.

In certain embodiments, the disease to be treated or prevented by the compositions of the invention is selected from the group consisting of a bacterial disease, a fungal disease, and a viral disease. As used herein, the terms "bacterial disease", "fungal disease" and "viral disease" refer to a disease caused by a bacterial pathogen, a fungal pathogen, or a viral pathogen, respectively. In a particular embodiment, the disease is a bacterial disease. Several pathogens are known in the art to be controlled by administration of bacterial compositions, for example, by administration of Bacillus species. For example, Baron (2009, Postgraduate Medicine 121(2): 1-5) teaches that administration of a probiotic comprising Bacillus coagulans to human subjects infected with influenza A or adenovirus significantly increased the subjects' immune response. Bastos et al. (2013, Viruses 5: 1219-1230).

Examples of pathogens that are known to be controlled by Bacillus species, and the corresponding diseases caused by these pathogens, are shown in Table 1A below.

TABLE 1A

Exemplary pathogens and corresponding diseases controlled by Bacillus species.

| Pathogen | Disease |
| --- | --- |
| Brachyspira hyodisenteriae | Intestinal or colonic spirochetosis, diarrhea and dysentery (e.g. in poultry and swine) |
| Escherichia coli | Urinary tract infections, epidemic diarrheal diseases and late respiratory disease |
| Salmonella enteritidis | Food poisoning and gastroenteritis |
| Salmonella typhimurium | Food poisoning and gastroenteritis |
| Staphylococcus aureus | Bovine mastitis, tick pyemia (enzootic staphylococcosis), abscesses, dermatitis, furunculosis, meningitis, osteomyelitis, food poisoning, wound suppuration, and bumblefoot (e.g. in poultry) |
| Streptococcus suis | Streptococcal meningitis and arthritis |
| Vibrio anguillarum | Cholera-like enteritis in birds, crustaceans, fish and mammals |
| Yersinia enterocolitica | Sporadic diarrhea |
| Flavobacterium columnare | Columnaris (e.g. in fish) |
| Aeromonas salmonicida | Furunculosis (e.g. in fish) |
| Clostridium perfringens | Necrotic enteritis |
| Adenovirus | Viral Respiratory Tract Infection (e.g in humans) |
| Influenza Virus | Influenza (e.g in humans) |

The invention also relates to a method of preventing or reducing infection with a pathogen in a subject susceptible to infection with the pathogen comprising administering to the subject an effective amount of a composition comprising a bacterial spore and a germinative compound as described herein, thereby preventing or reducing infection in the subject. In certain embodiments, the pathogen is a bacterium, a fungus, or a virus. In certain embodiments, the pathogen is selected from the group consisting of the pathogens listed in Table 1A.

In a particular embodiment, the disease to be treated or prevented by the compositions of the invention is necrotic enteritis. Necrotic enteritis is an acute or chronic enterotoxemia seen in chickens, turkeys and ducks, caused by Clostridium perfringens and characterised by a fibrinonecrotic enteritis, usually of the mid-small intestine. Mortality may be 5-50%, usually around 10%. Infection occurs by fecal-oral transmission. Spores of the causative organism are highly resistant. Predisposing factors include coccidiosis/coccidiasis, diet (high protein), high viscosity diets (often associated with high rye and wheat inclusions in the diet), contaminated feed and/or water, and other debilitating diseases. Signs of necrotic enteritis include depression, ruffled feathers, lack of appetite, closed eyes, immobility, dark coloured diarrhea, and sudden death. Symptoms also include lesions, small intestine (usually middle to distal) thickened and distended, intestinal mucosa with diptheritic membrane, intestinal contents that are dark brown with necrotic material, reflux of bile-stained liquid in the crop if upper small intestine affected. Affected birds tend to be dehydrated and to undergo rapid putrefaction.

A presumptive diagnosis may be made based on flock history and gross lesions. Confirmation is on the observation of abundant rods in smears from affected tissues and a good response to specific medication, usually in less than 48 hours. Standard treatments include penicillins (e.g. phenoxymethyl penicillin, amoxycillin), in drinking water, or Bacitracin in feed (e.g. 100 ppm).

In certain embodiments of any of the aforementioned methods, the subject is a human. In certain embodiments of any of the aforementioned methods, the subject is a non-human animal. In certain embodiments the subject is selected from the group consisting of chickens, turkeys and ducks. In certain embodiments the, subject is selected from the group consisting of fish, shrimp, or mollusks. In certain embodiments, the fish are selected from the group consisting of salmon, trout, cyprinids, pike, perch, bullheads, turbot and halibut.

EXAMPLES

The following examples are provided to illustrate the invention in accordance with the principles of this invention, but are not to be construed as limiting the invention in any way.

In the following Examples, the terms "GOSD" (Germination Optimized Spray Drying) and "GO+" refer to compositions in which a germinative optimizer (L-alanine unless specified otherwise) was spray dried with the particular *Bacillus* species indicated. Spores of *Bacillus* species were spray dried with L-alanine being introduced to the spore mass immediately prior to spray drying as a solution containing 0.044 grams of alanine per milliliter of distilled water.

The term "GO−" refers to compositions wherein the *Bacillus* species was similarly spray dried without a germinative compound being present.

Further, the following method was employed to determining spore germination in the Examples unless otherwise indicated. When spores are placed in nutrient solutions and begin to germinate they release dipicolinic acid and ions which results in darkening. This indicator of germination results in a decrease in the optical extinction of visible light by a spore suspension. The rate of germination was therefore determined by counting the proportion of phase dark/bright spores, and monitoring the decrease in optical density at 600 nm (O.D. 600) of germinating spore suspensions under a u.v.-visible spectrophotometer. This ratio was then converted to percent germination.

Example 1: Increased Germination of *B. subtilis* ENV 923 in an Intimate Mixture with L-Alanine In order to compare the germination rate of the spores of intimate mixtures this invention with that of spores conventionally employed in the absence of a germinant, the following treatments were performed:

A. Formation of an intimate mixture: Spores of *B. subtilis* ENV 923 were spray dried with L-alanine being introduced to the spore mass immediately prior to spray drying as a solution containing 0.044 grams of alanine per milliliter of distilled water. The intimate mixture produced was germinated by subsequent introduction in a solution consisting of 0.01 M phosphate buffer in distilled water with resultant pH 7.

B. Conventional mixing of spores with a germinant: Spores of *B. subtilis* ENV 923 were spray dried and subsequently introduced into a solution consisting of 0.01 M phosphate buffer in distilled water with resultant pH 7. Such spores were germinated by the introduction in a solution consisting of 0.01 M phosphate buffer in distilled water with resultant pH 7; plus 0.0001 grams of alanine per milliliter of solution.

C. Germination of spores alone: Spores of *B. subtilis* ENV 923 were spray dried and subsequently introduced into a solution consisting of 0.01 M phosphate buffer in distilled water with resultant pH 7.

Two replications of each such treatment were performed. Table 1B below shows the average results of such treatments affecting the germination of *B. subtilis* ENV 923 as measured by a percent drop in optical density. A drop in optical density indicates progression of germination. Optical density (OD) was measured at 600 nm wavelength with a Jenway Model 6320D Visible Range Spectrophotometer. L-alanine utilized was 99% purity and sourced from Alfa Aeser; Heysham, Lancashire, United Kingdom.

TABLE 1B

Percent reduction from OD (600 nm) baseline over time.

| Sample time (minutes) | 0 | 5 | 10 | 15 | 20 |
|---|---|---|---|---|---|
| Intimate Mixture | 0% | 2.7% | 17.7% | 34.3% | 41.2% |
| Conventional Mixing | 0% | 0.5% | 18.8% | 31.9% | 33.7% |
| Spores Alone | 0% | 1.3% | 3.2% | 4.1% | 7.5% |

The above results show that the spores which are formulated into an intimate mixture with a germinative compound through processes such as spray drying germinate more rapidly than do spores which are conventionally mixed with the same germinant. Thus plant propagation material coated with the composition of this invention will more rapidly and efficiently receive the benefits associated with the particular bacterium with which they are coated as such bacterium will be present in greatly enhanced amounts.

Example 2: Increased Germination of *Bacillus subtilis* Strain ENV923 Treated with GOSD

*Bacillus subtilis* spores were treated with GOSD (Germination Optimized Spray Drying) via spray drying spores in the presence of a solution of L-alanine, and germination levels were determined via Optical Density (OD) readings. 0.01 M Potassium Phosphate Buffer, pH 7

The 0.01M Potassium Phosphate buffer was prepared using 1M $K_2HPO_4$ (87.09 g dissolved in 0.5 L distilled water) and 1M $KH_2PO_4$ (68.045 g dissolved in 0.5 L distilled water) solutions. Combining 61.5 ml of 1M $K_2HPO_4$ with 38.5 ml 1 M $KH_2PO_4$ and diluting to 1000 ml with distilled water 0.1M Potassium Phosphate buffer at pH 7.0 was made. Further diluting the 0.1M Potassium Phosphate buffer with distilled water at the ration 1:10, the 0.01M Potassium Phosphate buffer, pH 7.0 was obtained. The buffer was sterilized by autoclaving at 121° C. for sixty (60) minutes.

*Bacillus subtilis* spore suspensions were prepared at the concentration $1.7 \times 10^8$ cfu/ml in 0.01 M Potassium Phosphate buffer, pH 7.0, incubated in the preheated 37° C. water bath, and evaluated for percent of germination in 5 minute intervals over a 45 minute period.

TABLE 2

% Germination of *Bacillus subtilis* ENV923 at 37° C. with and without GOSD treatment

| | Minutes | | | | | | | | | |
|---|---|---|---|---|---|---|---|---|---|---|
| | 0 | 5 | 10 | 15 | 20 | 25 | 30 | 35 | 40 | 45 |
| *B. subtilis* GOSD | 0 | 13% | 45% | 63% | 64% | 75% | 76% | 80% | 81% | 83% |
| *B. subtilis* Control | 0 | 7% | 9% | 10% | 11% | 14% | 14% | 16% | 18% | 19% |

Conclusion: GOSD treatment significantly enhanced the percent germination and speed of germination of *Bacillus subtilis* spores.

Example 3: Increased Germination of *Bacillus licheniformis* Strain ENV100 Treated with GOSD

*Bacillus licheniformis* spores were treated with GOSD via spray drying spores in the presence of 0.044 grams of L-alanine per mL of distilled water as described in Example 1. Germination levels were determined via Optical Density (OD) readings as described above using 0.01 M Potassium Phosphate buffer, pH 7.0 for spore suspension preparation.

*Bacillus licheniformis* spore suspensions were prepared at the concentration $1.29 \times 10^8$ cfu/ml in 0.01 M Potassium Phosphate buffer, pH 7.0, incubated in the preheated 37° C. water bath, and evaluated for percent of germination in five (5) minute intervals over a forty five (45) minute period.

TABLE 3

% Germination of *Bacillus licheniformis* treated and non-treated spore suspensions

| | Minutes | | | | | | | | | |
|---|---|---|---|---|---|---|---|---|---|---|
| | 0 | 5 | 10 | 15 | 20 | 25 | 30 | 35 | 40 | 45 |
| *B. licheniformis*, control | 0 | 1% | 5% | 3% | 10% | 11% | 10% | 10% | 10% | 10% |
| *B. licheniformis*, GOSD | 0 | 4% | 5% | 39% | 60% | 81% | 85% | 88% | 91% | 91% |

Conclusion: GOSD treatment significantly enhanced percent germination and speed of germination of *Bacillus licheniformis* spores.

Example 4: Increased Germination at Various pH Levels for *Bacillus subtilis* Strain ENV923 Treated with GOSD

*Bacillus subtilis* strain ENV923 GO+ and GO− spores were prepared as described above and re-suspended in 0.01 M Potassium Phosphate buffer at various pH levels. $OD_{600}$ measurements were performed as described above.

0.01M Potassium Phosphate Buffers at pH 3.0-7.0

0.01M Potassium Phosphate buffer, pH 7.0 buffer was prepared as described in Example 1.

To prepare 0.01M Potassium Phosphate buffers with pH range from 3.0 to 6.0 as base buffer was used 0.1M Potassium Phosphate buffer, pH 6.0 made by mixing 13.2 ml of 1M $K_2HPO_4$ and 86.8 ml of 1M $KH_2PO_4$ solutions (described in Example 1) and bringing the volume to 1 L with distilled water.

To obtain 0.01 M Potassium Phosphate buffers with pH 5.0 to pH 3.0, 0.1 M Potassium Phosphate buffer, pH 6.0 was diluted with distilled water, pH of buffers was lowered to pH 5.0, pH 4.0 and pH 3.0 using 1M $H_2PO_4$ and final volume brought up with distilled water keeping ratio of 0.1 M buffer to distilled water 1:10.

Prepared buffers were stored at 4° C. and prior to each experiment pH of buffers was re-adjusted using 1 M NaOH or 1 M $H_2PO_4$.

TABLE 4

Germination results with GOSD (GO+) and without GOSD (GO−) at various pH levels, table shows percent germination measured at 5 minute intervals.

| | Minutes | | | | | | | | | |
|---|---|---|---|---|---|---|---|---|---|---|
| | 0 | 5 | 10 | 15 | 20 | 25 | 30 | 35 | 40 | 45 |
| GO+ pH 7 | 0 | 8% | 48% | 69% | 80% | 84% | 88% | 90% | 91% | 92% |
| GO− pH 7 | 0 | 3% | 3% | 8% | 10% | 11% | 13% | 14% | 16% | 16% |
| GO+ pH 6 | 0 | 4% | 40% | 58% | 69% | 75% | 77% | 78% | 81% | 82% |
| GO− pH 6 | 0 | 1% | 4% | 5% | 9% | 8% | 11% | 13% | 12% | 12% |
| GO+ pH 5 | 0 | 7% | 24% | 34% | 39% | 41% | 43% | 45% | 46% | 46% |
| GO− pH 5 | 0 | 4% | 4% | 5% | 5% | 6% | 6% | 7% | 7% | 7% |
| GO+ pH 4 | 0 | 5% | 23% | 28% | 30% | 31% | 33% | 32% | 33% | 34% |
| GO− pH 4 | 0 | 3% | 4% | 5% | 4% | 4% | 5% | 3% | 4% | 4% |
| GO+ pH 3.5 | 0 | 5% | 11% | 16% | 18% | 18% | 18% | 18% | 20% | 20% |
| GO− pH 3.5 | 0 | 2% | 1% | 1% | 1% | 1% | 1% | 2% | 0% | 1% |
| GO+ pH 3 | 0 | 11% | 16% | 19% | 19% | 22% | 21% | 22% | 21% | 22% |
| GO− pH 3 | 0 | 4% | 4% | 4% | 5% | 2% | 3% | 4% | 2% | 4% |

Conclusion: Treatment with GOSD enables *Bacillus subtilis* spores to germinate faster and overcome the effects of lower pH levels.

Example 5: Increased Germination of *Bacillus subtilis* Strain ENV923 Treated with GOSD. Spore Germination Response as Affected by Various Temperature Levels. Table Shows Percent Germination Measured at 10 Minute Intervals

*Bacillus subtilis* strain ENV 923 GOSD and Control spores were prepared as described above. Germination of spores was tested via Optical Density (OD) measurements as described above. Spore suspensions for $OD_{600}$ measurements were prepared and cooled to 4° C. in 0.01 M Potassium Phosphate buffer, pH 7.0 (Phosphate buffer, pH 7.0 preparation) at the concentration $1.7 \times 10^8$ cfu/ml. For each spore suspension 3 culture tubes filled to 3 ml volume were prepared. Following agitation and initial $OD_{600}$ measurement the tubes were incubated in water baths preheated to 25° C., 30° C. and 37° C. for 120 min. At 10 min intervals tubes were agitated and $OD_{600}$ measurements taken.

agitation until completely dissolved. It was then aliquoted into bottles and autoclaved for 30 minutes at 121° C. Based on the manufacture's reported powder contents, the mTSB media contained per liter:
Pancreatic Digest of Casein: 28.3 mg
Papic Digest of Soybean: 5.0 mg
Dextrose: 4.2 mg
Sodium Chloride: 8.3 mg
Dipotassium Phosphate: 4.2 mg Sodium chloride (Amresco X190) was added to induce osmotic stress where appropriate such that the final concentrations were 0.5 M or 1.5 M (29.22 g/L and 87.66 g/L respectively) before the media was heated and autoclaved.
Spore Suspensions:

Spore powders of *Bacillus licheniformis* strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1 \times 10^{10}$ cfu/ml. From

TABLE 5

Percent germination of *Bacillus subtilis* with GO− and GO+ at 37° C., 30° C. and 25° C.

| | Minutes | | | | | | | | | | | | |
|---|---|---|---|---|---|---|---|---|---|---|---|---|---|
| | 0 | 10 | 20 | 30 | 40 | 50 | 60 | 70 | 80 | 90 | 100 | 110 | 120 |
| GO+, 37° C. | 0 | 36% | 58% | 63% | 68% | 70% | 70% | 71% | 70% | 70% | 70% | 70% | 70% |
| GO+, 30° C. | 0 | 12% | 32% | 45% | 52% | 55% | 58% | 59% | 58% | 60% | 60% | 60% | 60% |
| GO+, 25° C. | 0 | 1% | 9% | 16% | 23% | 28% | 32% | 33% | 35% | 37% | 36% | 35% | 35% |
| GO−, 37° C. | 0 | 1% | 4% | 6% | 7% | 9% | 9% | 9% | 9% | 9% | 9% | 9% | 9% |
| GO−, 30° C. | 0 | 0% | 2% | 3% | 4% | 6% | 6% | 7% | 7% | 8% | 9% | 8% | 7% |
| GO−, 25° C. | 0 | 0% | 2% | 3% | 4% | 5% | 7% | 8% | 8% | 9% | 10% | 10% | 10% |

Conclusion: Treatment with GOSD (GO+) enables *Bacillus subtilis* spores to germinate faster and overcome the effects of lower temperature regimes.

Example 6: Percent Germination of *Bacillus licheniformis* with and without GOSD in the Presence of Different Molar Solutions of NaCl Medium:

The medium was a dilute Tryptic Soy Broth (mTSB)(BD, 211822). The medium was prepared by suspending 50 mg of Tryptic Soy Broth powder in 1 L water with heat and this spore suspension, 250 µl was transferred to tubes containing 4.75 ml mTSB to give a final concentration of $5 \times 10^8$ cfu/ml. These concentrations are determined by optimizations performed on each batch of spores to achieve a starting OD600 of approximately 0.6.
OD Germination Assay:

Tubes containing the suspended spores were immediately vortexed, measured at OD600 for time point zero, and incubated in a 37° C. water bath. At respective time intervals, the time was recorded, tubes were removed, vortexed, measured at OD600 and returned to the water bath. The percent decrease in OD600 was determined by subtracting the measured value from the zero time point, divided by the zero time point and multiplied by 100%. Full germination was previously documented to correspond to a percent OD600 decrease of 60%. Therefore Percent Germination was determined by multiplying the percent OD600 decrease by 1.67.

TABLE 6

% Germination of *Bacillus licheniformis* spores over one hour with GOSD (GO+) and without (GO−) in the presence of 0, .5 Molar and 1.5 Molar solutions of NaCl.

| Time | GO+ 0M | GO− 0M | GO+ 0.5M | GO− 0.5M | GO+ 1.5M | GO− 1.5M |
|---|---|---|---|---|---|---|
| 0:00 | 0 | 0 | 0 | 0 | 0 | 0 |
| 0:11 | 7% | 0% | 29% | 1% | 15% | 2% |
| 0:16 | 23% | 0% | 49% | 0% | 30% | 0% |
| 0:22 | 44% | 3% | 61% | 0% | 44% | 0% |
| 0:27 | 53% | 0% | 67% | 0% | 48% | 0% | tion was made by suspending 2 g into 20 ml water, and 0.22 μm filtering. This was added to mTSB aliquots to achieve 0, 50, 100, and 200 ppm final concentrations.

Spore Suspensions:

Spore powders of *Bacillus licheniformis* strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $2\times10^9$ cfu/ml. From this spore suspension, 250 μl was transferred to tubes containing 4.75 ml mTSB to give a final concentration of $1\times10^8$ cfu/ml. These concentrations are determined by optimizations performed on each batch of spores to achieve a starting OD600 of approximately 0.6.

OD Germination Assay:

Performed and calculated as indicated in Example 6.

TABLE 7

Percent germination of *Bacillus licheniformis* spores over one hour with GOSD (GO+) and without (GO−) in the presence of 0, 50 ppm, 100 ppm and 200 ppm solutions of Copper ions.

| Time | GO+ 0 ppm | GO− 0 ppm | GO+ 50 ppm | GO− 50 ppm | GO+ 100 ppm | GO− 100 ppm | GO+ 200 ppm | GO− 200 ppm |
|---|---|---|---|---|---|---|---|---|
| 0:00 | 0.00 | 0.00 | 0.00 | 0.00 | 0.00 | 0.00 | 0.00 | 0.00 |
| 0:05 | 3.1% | 0.6% | 7.7% | 1.5% | 7.8% | 1.4% | 5.0% | 2.8% |
| 0:11 | 19.8% | 1.1% | 14.3% | 2.0% | 12.5% | 1.9% | 9.0% | 4.6% |
| 0:16 | 34.1% | 2.2% | 25.2% | 2.0% | 16.7% | 3.3% | 11.5% | 4.6% |
| 0:21 | 40.9% | 4.4% | 30.7% | 1.5% | 19.3% | 5.1% | 14.0% | 4.6% |
| 0:26 | 47.7% | 4.4% | 34.0% | 2.0% | 18.2% | 5.1% | 15.0% | 6.5% |
| 0:31 | 50.2% | 4.4% | 38.4% | 1.5% | 21.9% | 5.6% | 15.0% | 5.6% |
| 0:36 | 50.8% | 4.4% | 38.9% | 0.5% | 20.8% | 6.1% | 17.0% | 6.0% |
| 0:41 | 52.0% | 3.3% | 40.6% | 1.5% | 21.4% | 6.5% | 18.0% | 5.6% |
| 0:47 | 55.8% | 3.9% | 45.0% | 3.0% | 26.0% | 7.5% | 20.0% | 6.0% |
| 0:53 | 57.0% | 2.8% | 44.4% | 2.5% | 25.5% | 8.4% | 19.5% | 6.0% |
| 0:58 | 57.6% | 3.9% | 45.5% | 3.0% | 25.0% | 8.4% | 20.5% | 6.9% |
| 1:04 | 60.1% | 4.4% | 45.0% | 1.0% | 24.5% | 8.4% | 21.0% | 4.6% |

TABLE 6-continued

% Germination of *Bacillus licheniformis* spores over one hour with GOSD (GO+) and without (GO−) in the presence of 0, .5 Molar and 1.5 Molar solutions of NaCl.

| Time | GO+ 0M | GO− 0M | GO+ 0.5M | GO− 0.5M | GO+ 1.5M | GO− 1.5M |
|---|---|---|---|---|---|---|
| 0:32 | 59% | 0% | 70% | 1% | 53% | 0% |
| 0:38 | 64% | 0% | 74% | 1% | 56% | 0% |
| 0:43 | 68% | 0% | 75% | 0% | 58% | 0% |
| 0:49 | 71% | 0% | 77% | 0% | 61% | 0% |
| 0:55 | 72% | 0% | 77% | 2% | 63% | 0% |
| 1:01 | 75% | 0% | 78% | 2% | 66% | 0% |

Conclusion: Treatment with GOSD enables *Bacillus licheniformis* spores to germinate faster and overcome the osmotic stress effects of various salt (NaCl) levels.

Example 7: Percent Germination of *Bacillus licheniformis* with and without GOSD in the Presence of Different Part Per Million Solutions of Copper Medium:

mTSB medium was prepared as above, but supplemented with NaCl to a final concentration of 50 mM to create an osmotically balanced media. A $1\times10^5$ ppm Copper (II) nitrate hemi(pentahydrate) (Alfa Aesar 12523) stock solu- Conclusion: Treatment with GOSD enables *Bacillus licheniformis* spores to germinate faster and overcome the stress effects of various levels of Copper ions.

Example 8: Percent Germination of *Bacillus licheniformis* with and without GOSD in the Presence of Different Part Per Million Solutions of Aluminum Medium:

mTSB medium was prepared as above, but supplemented with NaCl to a final concentration of 50 mM to create an osmotically balanced media. A 1000 ppm $Al^{3+}$ stock solution was made by suspending 0.62 g of $Al_2(SO_4)_3$*14 $H_2O$ (Alfa Aesar 12362) into 50 ml water, and 0.22 μm filtering. This was added to mTSB aliquots to achieve 0, 0.25, 0.50, and 1.0 ppm final concentrations. The pH of the media was then brought down to pH 4.5 by the addition of HCl to allow complete separation of the $Al^{3+}$ ion.

Spore Suspensions:

Spore powders of *Bacillus licheniformis* strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1\times10^{10}$ cfu/ml. From this spore suspension, 250 μl was transferred to tubes containing 4.75 ml mTSB to give a final concentration of $5\times10^8$ cfu/ml. These concentrations are determined by optimizations performed on each batch of spores to achieve a starting OD600 of approximately 0.6.

OD Germination Assay:

Performed and calculated as in Example 6.

TABLE 8

Percent germination of *Bacillus licheniformis* spores over one hour with GOSD (GO+) and without (GO−) in the presence of 0, 0.25 ppm, 0.50 ppm and 1.0 ppm solutions of Aluminum ions.

| Time | GO+ 0 ppm | GO− 0 ppm | GO+ 0.25 ppm | GO− 0.25 ppm | GO+ 0.50 ppm | GO− 0.50 ppm | GO+ 1.00 ppm | GO− 1.00 ppm |
|---|---|---|---|---|---|---|---|---|
| 0:00 | 0 | 0 | 0 | 0 | 0 | 0 | 0 | 0 |
| 0:07 | 21% | 2% | 9% | 1% | 26% | 2% | 30% | 3% |
| 0:14 | 48% | 3% | 47% | 4% | 50% | 4% | 52% | 3% |
| 0:22 | 62% | 3% | 60% | 5% | 63% | 4% | 63% | 4% |
| 0:30 | 67% | 2% | 66% | 4% | 67% | 4% | 67% | 3% |
| 0:37 | 70% | 3% | 68% | 5% | 70% | 4% | 70% | 3% |
| 0:44 | 71% | 3% | 69% | 4% | 71% | 4% | 71% | 3% |
| 0:52 | 72% | 3% | 70% | 4% | 72% | 5% | 71% | 3% |
| 0:59 | 72% | 3% | 70% | 5% | 74% | 6% | 73% | 4% |
| 1:07 | 72% | 3% | 72% | 5% | 74% | 5% | 72% | 4% |

Conclusion: Treatment with GOSD enables *Bacillus licheniformis* spores to germinate faster and overcome the stress effects of various levels of Aluminum ions.

Example 9: Percent Germination of *Bacillus licheniformis* with and without GOSD in the Presence of Different Millimolar Solutions of Bile Salts Medium:

mTSB medium was prepared as above, but supplemented with NaCl to a final concentration of 50 mM to create an osmotically balanced media. A 80 mM bile salts stock solution was made by suspending 2.5 g sodium taurodeoxycholate (Sigma T0875), 1.1 g sodium glycodeoxycholate (Sigma G9910), and 0.346 g sodium deoxycholate (Sigma D5670) into 100 ml water, and 0.22 μm filtering. This was added to mTSB aliquots to achieve 0, 4, 6, and 8 mM final concentrations.

Spore Suspensions:

Spore powders of *Bacillus licheniformis* strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually. This was performed such that the final concentration in the blender jar was $1\times10^{10}$ cfu/ml. From this spore suspension, 250 μl was transferred to tubes containing 4.75 ml mTSB to give a final concentration of $5\times10^{8}$ cfu/ml. These concentrations are determined by optimizations performed on each batch of spores to achieve a starting OD600 of approximately 0.6.

OD Germination Assay:

Performed and calculated as above.

TABLE 9

Percent germination of *Bacillus licheniformis* spores over one hour with GOSD (GO+) and without (GO−) in the presence of 0, 4 mM, 6 mM and 8 mM ppm solutions of Bile Salts.

| Time | GO+ 0 mM | GO− 0 mM | GO+ 4 mM | GO− 4 mM | GO+ 6 mM | GO− 6 mM | GO+ 8 mM | GO− 8 mM |
|---|---|---|---|---|---|---|---|---|
| 0:00 | 0 | 0 | 0 | 0 | 0 | 0 | 0 | 0 |
| 0:05 | 13% | 4% | 17% | 1% | 22% | 1% | 29% | 7% |
| 0:10 | 44% | 5% | 44% | 1% | 50% | 2% | 56% | 10% |
| 0:15 | 61% | 5% | 61% | 1% | 62% | 1% | 67% | 9% |
| 0:20 | 70% | 5% | 69% | 2% | 70% | 3% | 73% | 11% |
| 0:26 | 76% | 5% | 73% | 2% | 75% | 2% | 77% | 11% |
| 0:31 | 78% | 5% | 77% | 3% | 78% | 3% | 81% | 11% |
| 0:36 | 81% | 5% | 80% | 2% | 80% | 3% | 83% | 11% |
| 0:41 | 83% | 6% | 82% | 3% | 82% | 2% | 84% | 11% |
| 0:46 | 85% | 7% | 83% | 2% | 84% | 2% | 86% | 11% |
| 0:51 | 86% | 6% | 85% | 2% | 86% | 3% | 87% | 11% |
| 0:56 | 86% | 6% | 85% | 2% | 87% | 3% | 88% | 11% |
| 1:01 | 87% | 6% | 87% | 2% | 88% | 3% | 90% | 11% |
| 1:06 | 88% | 7% | 89% | 3% | 89% | 3% | 90% | 11% |

Conclusion: Treatment with GOSD enables *Bacillus licheniformis* spores to germinate faster and overcome the stress effects of various levels of bile salts which can be encountered in a gastrointestinal tract.

Example 10: Average Growth of Three Replicates of *Bacillus licheniformis* with or without GOSD in Defined Potassium Phosphate Medium and 2% Glucose

*Bacillus licheniformis* strain ENV 431 GO+ spores were treated with GOSD (procedure described earlier). As a control were used GO− spores from the same culture that were spray dried without using GOSD. The growth test was performed in Minimal Salts Medium supplemented with 2% glucose.

Medium

The medium was prepared by dissolving $(NH_4)_2SO_4$ (1.26 g/L), $MgCl_2$ (0.81 g/L), $CaCl_2$ (0.15 g/L), NaCl (0.05 g/L) in distilled water and adding 1 ml/L 1000× Trace Mineral Mix ($MnSO_4$ (0.85 g/50 ml), $ZnSO_4$ (0.15 g/50 ml), $FeSO_4 \times 7H_2O$ (0.15 g/50 ml), Thiamino-hydrochloride (0.05 g/50 ml). Prepared solution was poured into flasks (90 ml/flask) and autoclaved at 121° C. for 40 min. Before inoculation the medium was supplemented with 4 ml of filter sterilized solution of 25× Potassium Phosphate ($K_2HPO_4$ (3.44 g/50 ml), $KH_2PO_4$ (2.81 g/50 ml)) and 2 ml of 50×(100 g/200 ml) glucose to 2% final concentration.

Growth of *Bacillus licheniformis* Cells

Amount of spores used for inoculation was determined using GO− and GO+ spore powder counts. Concentrated (1000×) *Bacillus licheniformis* strain ENV 431 spore suspensions were prepared by blending spores in the sterile blender jars using sterile water and added to the flasks with medium to the concentrations indicated in the table below as 0 h. The counts of initial culture were obtained by performing dilutions and plate counts of blended spore suspensions. There were 3 flasks prepared for each spore sample.

The flasks were incubated at 30° C., 150 rpm and grown for 48 h. The samples were taken and plate counts done at 24 h and 48 h.

TABLE 10

Average growth of three replicates of *Bacillus licheniformis* with GOSD (GO+) or without GOSD (GO−) in minimal potassium phosphate medium and 2% glucose. Data shown is in cfu/ml.

|  | 0 hour | 24 hours | 48 hours |
|---|---|---|---|
| *B. licheniformis* GO− | $1.88 \times 10^3$ | $2.20 \times 10^4$ | $9.4 \times 10^4$ |
| *B. licheniformis* GO+ | $1.46 \times 10^3$ | $7.95 \times 10^4$ | $3.65 \times 10^5$ |

Conclusion: GOSD treatment significantly enhanced *Bacillus licheniformis* germination and growth rate.

Example 11: Growth of *Bacillus licheniformis* Over a Two Day Period; Comparing Treatments with or without GOSD in the Presence of Different Concentrations of NaCl Medium:

mTSB was prepared as above, but with sodium chloride (Amresco X190) added to induce osmotic stress where appropriate such that the final concentrations were 0, 0.5, 1.0, or 1.5 M (0, 29.22, 58.44, or 87.66 g/L respectively). The media was heated, aliquoted to flasks, and autoclaved.

Plate Count Agar (PCA) (BD 247910) was prepared according to the manufacturer's instructions: 23.5 g of powder suspended in 1 L of water, bring to boil with frequent agitation, aliquot into glass jars, and autoclave. Media jars were cooled in a 45° C. water bath until needed. The manufacturer of the powder reports the following contents for PCA per liter:
Pancreatic Digest of Casein: 5.0 g
Yeast Extract: 2.5 g
Dextrose: 1.0 g
Agar: 15.0 g
Spore Suspensions:

Spore powders of *Bacillus licheniformis* strain ENV100 treated or not treated with GOSD were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually followed by serial dilutions in sterile water. This was performed such that the final concentration in the culture flasks was $1 \times 10^2$ cfu/ml.
Quantification:

Flasks were incubated at 37° C. shaking at 150 rpm for 28 hours ("1 day") or 50 hours ("2 days"). Aliquots from each flask were serially diluted into petri dishes with PCA cooled to <45° C. poured on top, swirled, and allowed to solidify.

Plates were inverted and incubated for approximately 24 hours at 37° C. Colonies were counted and concentrations calculated based on dilutions. Approximately 10 μl samples from each flask were also streaked on PCA plates to test for purity.

TABLE 11

Growth of *Bacillus licheniformis* treated with GOSD (GO+) when challenged by osmotic stress from salt solution.

| Day | GO+ or − | Molar | cfu/ml |
|---|---|---|---|
| 1 | GO+ | 0 | 1.05E+06 |
| 1 | GO− | 0 | 7.33E+03 |
| 1 | GO+ | 0.5 | 3.60E+06 |
| 1 | GO− | 0.5 | 5.00E+06 |
| 1 | GO+ | 1.0 | 3.00E+05 |
| 1 | GO− | 1.0 | 2.31E+05 |
| 1 | GO+ | 1.5 | 1.22E+04 |
| 1 | GO− | 1.5 | 1.50E+02 |
| 2 | GO+ | 0 | 8.17E+06 |
| 2 | GO− | 0 | 4.90E+05 |
| 2 | GO+ | 0.5 | 7.03E+06 |
| 2 | GO− | 0.5 | 8.43E+06 |
| 2 | GO+ | 1.0 | 2.07E+06 |
| 2 | GO− | 1.0 | 3.50E+06 |
| 2 | GO+ | 1.5 | 4.33E+05 |
| 2 | GO− | 1.5 | 1.53E+02 |

Conclusion: GOSD treatment significantly enhanced germination and growth of *Bacillus licheniformis* under osmotic salt stress.

Example 12: Protease Activity of *Bacillus subtilis* Strain ENV 923

*Bacillus subtilis* strain ENV 923 spores treated with GOSD (GO+) as described earlier, and non-treated (GO−) were used for the protease activity test.

Medium

Chemically Defined Salt Medium (CDSM) was used for cell propagation in a protease test. Medium was prepared by dissolving base solution components (g/L): $(NH_4)SO_4$, 1.26 g; L-glutamic acid, 1.18 g; $MgCl_2$, 0.81; $CaCl_2$, 0.155 and 85% L-lactic acid (0.530 ml/L) in distilled water and adding 1 ml/L of 1000× Trace Mineral Mix (g/50 ml). Flasks with base solution (48 ml/flask) were autoclaved for 40 min. Before inoculation 2 ml of separately prepared filter sterilized 25× buffer solution with glucose (g/50 ml): MOPS, 11.6; $KH_2PO_4$, 0.6; glucose, 4.5 were added.

Growth of *Bacillus subtilis* ENV923 Cells

The amount of spores used for inoculation was determined using GO− and GO+ spore powder counts. Concentrated (1000×) *Bacillus subtilis* strain ENV923 spore suspensions were prepared by blending spores in the sterile blender jars using sterile 0.01 M Potassium Phosphate buffer, pH 7.0 and added to the flasks at the concentration of about $1 \times 10^4$ cfu/ml. The counts of initial culture were confirmed by performing dilutions and plate counts of blended spore suspensions. There were 3 flasks prepared for each spore sample.

The flasks were incubated at 30° C., 150 rpm, and samples were taken at 48 h.

Protease Activity Assay

Protease activity assay was carried out on cell supernatants using casein as substrate and Folin & Ciocalateu's Phenol reagent that reacts with tyrosine and facilitates blue color development. Protease activity unit was defined as amount of enzyme that liberates 1 µg of tyrosine in one minute. Amount of tyrosine in test tubes was determined by measuring $OD_{650}$ in a Jenway 7305 spectrophotometer and calculating liberated tyrosine using a standard curve.

Reagents

Reagent 1: 0.05 M Potassium Phosphate Buffer, pH 7.0

0.1 M Potassium Phosphate buffer, pH 7.0 (prepared as described in Example 1) was diluted to at the ratio 1:1 with distilled water to obtain 0.05 M Potassium Phosphate buffer, pH 7.0

Reagent 2: 0.65% Casein Solution 0.65 g of casein were dissolved in 80 ml of 0.05 M Potassium Phosphate buffer, pH 7.0, heated to bring casein into solution, and the final volume brought to 100 ml with 0.05 M Potassium Phosphate buffer, pH 7.0.

Reagent 3: 15% Trichloroacetic Acid (TCA)

15 g of TCA were dissolved in distilled water and the final volume brought to 100 ml.

Reagent 4: 20% $Na_2CO_3$ 20 g of $Na_2CO_3$ dissolved in distilled water and final volume brought to 100 ml.

Protease Assay 10 ml of culture were centrifuged and supernatant filtered through 0.2 µm filter into sterile tubes.

3 ml of filtered supernatant were mixed with 3 ml of 0.65% casein solution and put into 37° C. water bath for 1 h.

Reaction was stopped by adding 6 ml of 15% TCA and samples centrifuged for 5 min.

0.5 ml of each sample was mixed with 1 ml of 20% $Na_2CO_3$, followed by 0.5 ml of Folin & Ciolcallieu's Phenol reagent addition and incubation for 20 min at room temperature to allow blue color development.

3 ml of distilled water were added to each sample and after mixing the $OD_{650}$ was measured.

To calculate protease activity the standard curve for tyrosine was prepared obtaining dilution series of tyrosine dissolved in distilled water, treating them to the same conditions as the culture samples, and measuring $OD_{650}$.

TABLE 12

Protease production of Bacillus subtilis treated with GOSD (GO+) versus control (GO−)

| Bacillus subtilis | | Protease activity units |
|---|---|---|
| 54 h. | GO+ | 71.5 |
| | GO− | 40 |

Conclusion: Treatment of Bacillus subtilis spores with GOSD enables greater production of enzymes such as protease.

Example 13: Germination of Streptomyces viridochromogenes in the Presence of Germinative Compounds Streptomyces viridochromogenes spores were harvested from plates by pouring 10 ml of TX buffer (0.05 M Tris-HCl buffer, pH 7.3 with 0.001% Tween 80) and removing the spores with a sterile cotton swab. Spore suspensions from plates were poured into sterile 50 ml tubes. When spore suspensions of all samples were obtained, heat shock was performed by putting the tubes with spore suspensions into a heat block, allowing the temperature to reach 55° C., and maintain the temperature at 55° C. for 10 min. After heat shock spore suspensions were cooled in ice water for 5 min and spun down for 30 min. Supernatant was poured off, spores re-suspended in 25 ml 0.02 M Potassium Phosphate buffer, pH 7.0 at 4° C. and spun down for 15 min. After pouring off supernatant, spores were re-suspended in 20 ml of 0.02 M Potassium Phosphate buffer, pH 7.0 and vigorously mixed to obtain the spore suspension that was used in the experiment.

Samples were prepared by mixing 1.5 ml of 2× germinant blend with 1.5 ml spore suspension. All germinant blends were prepared in distilled water as 2×50 ml solutions. Calcium chloride was prepared as a 100× solution (0.4 g/10 ml) and 20 µl were added to 10 ml of 2× germinant blends. The final concentrations of the germinative compounds were as follows: 0.89 mg/ml of L-alanine; 1.17 mg/ml of L-valine, 13.2 mg/ml of L-asparagine; 2.25 mg/ml of glucose; and 2.25 mg/ml of fructose. After measuring initial OD600, samples were transferred to a 30° C. water bath and OD600 was measured at 15 min intervals for 90 min to determine germination rates.

TABLE 13

ENV 151 (Streptomyces viridochromogenes) % Reduction in Optical Density

| Ion/Germinant treatment | 0 | 15 | 30 | 45 | 60 | 75 | 90 |
|---|---|---|---|---|---|---|---|
| 0.01M KPO4 | 0 | 1.0% | 2.0% | 5.4% | 6.2% | 4.9% | 5.4% |
| 0.01M KPO4, $CaCl_2$ | 0 | 7.3% | 3.4% | 6.1% | 6.1% | 8.0% | 9.3% |
| 0.01M KPO4, $CaCl_2$, L-Ala | 0 | 1.8% | 5.2% | 12.2% | 11.9% | 14.2% | 17.6% |
| 0.01M KPO4, $CaCl_2$, L-Val | 0 | 2.0% | 4.9% | 11.2% | 7.8% | 14.4% | 18.0% |
| 0.01M KPO4, $CaCl_2$, L-Asn | 0 | 2.0% | 6.1% | 8.8% | 11.7% | 8.0% | 9.0% |
| 0.01M KPO4, $CaCl_2$, L-Ala, L-Asn | 0 | 7.7% | 12.1% | 14.4% | 19.8% | 20.4% | 18.6% |
| 0.01M KPO4, $CaCl_2$, L-Ala, L-Asn, glucose | 0 | 8.2% | 11.7% | 14.5% | 20.1% | 19.4% | 20.7% |
| 0.01M KPO4, $CaCl_2$, glucose | 0 | 7.0% | 8.8% | 7.0% | 10.5% | 12.6% | 13.2% |
| 0.01M KPO4, $CaCl_2$, glucose, fructose | 0 | 5.9% | 8.3% | 12.0% | 12.7% | 14.6% | 14.6% |
| 0.01M KPO4, $CaCl_2$, L-Ala, L-Asn, glucose, fructose | 0 | 11.7% | 14.0% | 17.7% | 20.4% | 22.2% | 22.4% |

Conclusion: Treatment of *Streptomyces viridochromogenes* spores with germinative compounds enhanced germination.

Example 14: Comparison of Germination Rates Between Intimate Mixtures and Conventional Mixing of Bacterial Spores and Germinative Compounds In order to compare the germination rate of the spores of intimate mixtures with that of spores conventionally mixed with a germinant, the following treatments are performed:
A. Formation of an intimate mixture: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus*, and *Streptomyces aureofacien* are dried with L-alanine, L-valine, L-proline, L-leucine, L-cysteine, L-threonine, L-glutamine, L-asparagine or L-phenylalanine being introduced to the spore mass immediately prior to drying as a solution containing 0.044 grams of the amino acid per milliliter of distilled water. The intimate mixture produced is germinated by subsequent introduction in a solution consisting of 0.01 M phosphate buffer in distilled water with resultant pH 7.
B. Conventional mixing of spores with a germinant: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus*, and *Streptomyces aureofacien* are hydrated and dried. Such spores are germinated by the introduction in a solution consisting of 0.01 M phosphate buffer in distilled water with resultant pH 7, and 0.0001 grams of L-alanine, L-valine, L-proline, L-leucine, L-cysteine, L-threonine, L-glutamine, L-asparagine or L-phenylalanine per milliliter of solution.
C. Germination of spores alone: Spores of *B. subtilis, B. amyloliquefaciens, B. brevis, B. cereus, B. coagulans, B. firmus, B. laterosporus, B. licheniformis, B. megaterium, B. mycoides, B. popilliae, B. polymyxa, B. pumilus, B. thuringiensis, Pasteuria penetrans, Pasteuria thornei, Pasteuria nishizawae, Streptomyces viridochromogenes, Streptomyces griseoviridis, Streptomyces lydicus, Streptomyces plicatus, Streptomyces sindeneusis, Streptomyces rochei, Streptomyces alni, Streptomyces viridis, Streptomyces thermovulgaris, Streptomyces griseus, Streptomyces acidiscabies, Steptomyces aureofaciens, Streptomyces galbus, Streptomyces microflavus*, and *Streptomyces aureofacien* are hydrated and dried. The spores are subsequently introduced into a solution consisting of 0.01 M phosphate buffer in distilled water with resultant pH 7.

The germination of spores resulting for each such treatment is measured by the percent drop in optical density or by counting the number of germinated spores under a microscope. It is found that the intimately mixed compositions germinate more rapidly than their corresponding conventionally mixed equivalent.

Example 15: Treatment of Maize Leaves, Carrot Root and Potato Tubers with *Bacillus Licheniformis* Spore Germinative Compound Mixtures To prepared the *Bacillus licheniformis* spore germinative compound mixtures, a solution of 0.044 g L-alanine per ml of distilled water was introduced to a *Bacillus licheniformis* spore mass, and the mixture was immediately spray dried. The resultant spray dried powder containing the intimate mixture of *Bacillus* spores and L-alanine is referred to as "GO+" in the treatments below. The *Bacillus* spores were also spray dried without the addition of L-alanine for use as a control. The spray dried *Bacillus* spores without the addition of L-alanine are described as "GO−" in the treatments below.

Before resuspending the spray dried *Bacillus licheniformis* spores, the bacterial count of the GO+ and GO− formulations was determined to adjust for differences in spore concentration as shown in Table 14 below.

TABLE 14

Bacterial counts in spray dried GO+ and GO− formulations of *B. licheniformis* spores

| Spore powder | Bacterial Count | Amount used per 1 ml suspension |
|---|---|---|
| GO+: *B. licheniformis* spray dry mix with L-alanine | $6.9 \times 10^{11}$ cfu/g | 0.018 gram |
| GO−: *B. licheniformis* spray dry, no L-alanine | $1.29 \times 10^{12}$ cfu/g | 0.009 gram |

The spray dried spores were suspended in 0.01 M Potassium Phosphate buffer at pH 7.0 which had been cooled to 4° C. before adding the spores. As shown in Table 14, the GO+ and GO− spray dried formulations were added to the buffer at a concentration of 0.018 g/ml and 0.009 g/ml, respectively, to adjust for differences in the concentration of spores in each formulation.

Maize (*Zea mays*) leaves were obtained from plants growing in a field. Each leaf was cut into approximately 2.5 cm sections. Carrot (*Daucus carota*) roots and potato (*Solanum tuberosum*) tubers were cut into sections with the outer skin remaining. The plant samples were placed on wet filter paper in a Petri dish with one plant sample per Petri dish. Approximately 150 μl of spore suspension was added to each plant sample. For the carrot and potato samples, the spore suspension was applied to the skin surface, i.e. the outer surface of the root or tuber. The petri dishes containing the plant samples were covered and incubated at 37° C. Samples for the 0 min. cell count were taken from the tubes of spore suspension. Subsequent samples were taken from the treated leaf sections at teach time point (15 min., 30 min. and 60 min.) and observed under a phase contrast microscope. Phase bright and phase dark spores numbers were obtained by taking pictures of a few observation fields and counting dark and bright cells. Spore germination level was determined based on the number of phase bright (not germinating) and phase dark (germinating)) spores under the phase contrast microscope.

As shown in Table 15 below, the percentage of germinating spores on the maize leaves treated with formulations containing L-alanine (GO+) were much higher than formulations without L-alanine (GO−). For example, 94% of the GO+ spores germinated in 30 min., while less than 20% of the GO− spores had germinated even after 60 min. Similar results were observed for carrot roots (Table 16) and potato tubers (Table 17). These results indicate that addition of L-alanine to the spray dried formulations resulted in faster germination of the spores on plant surfaces.

TABLE 15

Germination of *B. licheniformis* with L-alanine (GO+) or without L-alanine (GO−) on maize leaves. "Rep" is replicate, "Avg." is average.

| | GO− | | | | | | GO+ | | | | | |
|---|---|---|---|---|---|---|---|---|---|---|---|---|
| Time | Bright cells | | Dark cells | | Total | % of phase dark | Bright cells | | Dark cells | | Total | % of phase dark |
| (min) | Rep | Avg. | Rep | Avg. | cell # | cells | Rep | Avg. | Rep | Avg. | cell # | cells |
| 0 | 171 | 185.7 | 9 | 13.3 | 199.0 | 7.18 | 197 | 231.33 | 24 | 27.67 | 259 | 10.68 |
| | 171 | | 13 | | | | 243 | | 13 | | | |
| | 215 | | 18 | | | | 254 | | 46 | | | |
| 15 | 318 | 309.5 | 25 | 41.6 | 351.1 | 11.85 | 42 | 39 | 218 | 185.4 | 224.4 | 82.62 |
| | 284 | | 31 | | | | 46 | | 204 | | | |
| | 459 | | 53 | | | | 30 | | 133 | | | |
| | 495 | | 58 | | | | 41 | | 221 | | | |
| | 301 | | 41 | | | | 36 | | 151 | | | |
| 30 | 385 | 462 | 41 | 43.6 | 505.6 | 8.62 | 14 | 18.33 | 352 | 297.67 | 316 | 94.20 |
| | 388 | | 42 | | | | 12 | | 315 | | | |
| | 488 | | 44 | | | | 23 | | 268 | | | |
| | 488 | | 39 | | | | 14 | | 219 | | | |
| | 561 | | 52 | | | | 16 | | 280 | | | |
| | | | | | | | 31 | | 352 | | | |
| 60 | 243 | 320 | 56 | 66.5 | 386.5 | 17.21 | 10 | 10.2 | 259 | 317.2 | 327.4 | 96.88 |
| | 232 | | 56 | | | | 11 | | 316 | | | |
| | 380 | | 64 | | | | 12 | | 319 | | | |
| | 425 | | 90 | | | | 10 | | 339 | | | |
| | | | | | | | 8 | | 353 | | | |

TABLE 16

Germination of *B. licheniformis* with L-alanine (GO+) or without L-alanine (GO−) on carrot roots. "Rep" is replicate, "Avg." is average.

| | GO− | | | | | | GO+ | | | | | |
|---|---|---|---|---|---|---|---|---|---|---|---|---|
| Time | Bright spores | | Dark spores | | Total | % of phase dark | Bright spores | | Dark spores | | Total | % of phase dark |
| (min) | Rep | Avg. | Rep | Avg. | spore # | spores | Rep | Avg. | Rep | Avg. | spore # | spores |
| 0 | 183 | 217 | 18 | 33.8 | 250.8 | 13.48 | 217 | 221.2 | 28 | 28.8 | 250 | 11.52 |
| | 131 | | 34 | | | | 118 | | 28 | | | |
| | 233 | | 22 | | | | 299 | | 40 | | | |
| | 252 | | 40 | | | | 167 | | 21 | | | |
| | 286 | | 55 | | | | 305 | | 27 | | | |
| 15 | 318 | 260.33 | 61 | 48.17 | 308.5 | 15.61 | 176 | 203.83 | 115 | 179.5 | 383.3 | 46.83 |
| | 482 | | 69 | | | | 150 | | 122 | | | |
| | 226 | | 40 | | | | 254 | | 158 | | | |
| | 158 | | 37 | | | | 300 | | 241 | | | |
| | 167 | | 34 | | | | 204 | | 210 | | | |
| | 211 | | 48 | | | | 139 | | 231 | | | |
| 30 | 212 | 227.25 | 61 | 65.5 | 292.75 | 22.37 | 127 | 118.83 | 398 | 405.67 | 524.5 | 77.34 |
| | 220 | | 40 | | | | 129 | | 417 | | | |
| | 295 | | 90 | | | | 141 | | 409 | | | |
| | 182 | | 71 | | | | 95 | | 384 | | | |
| | | | | | | | 133 | | 428 | | | |
| | | | | | | | 88 | | 398 | | | |
| 60 | 287 | 250.5 | 83 | 75.5 | 326 | 23.16 | 80 | 75.33 | 603 | 621.83 | 697.2 | 89.20 |
| | 285 | | 103 | | | | 91 | | 859 | | | |
| | 198 | | 57 | | | | 61 | | 464 | | | |
| | 201 | | 60 | | | | 89 | | 885 | | | |
| | 319 | | 86 | | | | 69 | | 472 | | | |
| | 213 | | 64 | | | | 62 | | 448 | | | |

TABLE 17

Germination of B. licheniformis with L-alanine (GO+) or without L-alanine (GO−) on potato tubers. "Rep" is replicate, "Avg." is average.

| | GO− | | | | | | GO+ | | | | |
|---|---|---|---|---|---|---|---|---|---|---|---|
| | Bright cells | | Dark cells | | | % of phase | Bright cells | | Dark cells | | | % of phase |
| Time (min) | Rep | Avg. | Rep | Avg. | Total cell # | dark | Rep | Avg. | Rep | Avg. | Total cell # | dark |
| 0 | 414 | 397.5 | 12 | 14.5 | 412 | 3.65 | 504 | 608 | 19 | 20 | 628 | 3.29 |
|  | 381 |  | 17 |  |  |  | 712 |  | 21 |  |  |  |
| 15 | 399 | 565.5 | 69 | 67 | 633 | 10.59 | 432 | 541.33 | 163 | 214.33 | 755.7 | 28.36 |
|  | 481 |  | 88 |  |  |  | 737 |  | 262 |  |  |  |
|  | 738 |  | 56 |  |  |  | 731 |  | 263 |  |  |  |
|  | 696 |  | 60 |  |  |  | 558 |  | 234 |  |  |  |
|  | 647 |  | 71 |  |  |  | 449 |  | 201 |  |  |  |
|  | 432 |  | 58 |  |  |  | 341 |  | 163 |  |  |  |
| 30 | 500 | 555.33 | 84 | 95.67 | 651 | 14.70 | 247 | 203.5 | 390 | 392.5 | 596 | 65.86 |
|  | 496 |  | 126 |  |  |  | 222 |  | 458 |  |  |  |
|  | 747 |  | 121 |  |  |  | 250 |  | 381 |  |  |  |
|  | 554 |  | 78 |  |  |  | 119 |  | 386 |  |  |  |
|  | 479 |  | 78 |  |  |  | 218 |  | 364 |  |  |  |
|  | 556 |  | 87 |  |  |  | 165 |  | 376 |  |  |  |
| 60 | 452 | 304.67 | 70 | 71.67 | 316 | 22.65 | 44 | 31.33 | 245 | 271.5 | 302.8 | 89.65 |
|  | 293 |  | 80 |  |  |  | 16 |  | 225 |  |  |  |
|  | 304 |  | 75 |  |  |  | 37 |  | 275 |  |  |  |
|  | 270 |  | 68 |  |  |  | 27 |  | 271 |  |  |  |
|  | 261 |  | 72 |  |  |  | 38 |  | 284 |  |  |  |
|  | 248 |  | 65 |  |  |  | 26 |  | 329 |  |  |  |

Example 16: Evaluation of Germination, Plant Growth, and Yield for Maize Seeds Coated with a Composition Comprising a Bacterial Spore and a Germinative Compound Maize seeds are coated with compositions comprising various combinations of the bacterial spores and germinative compounds listed in Example 14. Seed coating is performed by conventional means, such as those described in U.S. Pat. No. 7,989,391 and U.S. Pat. No. 5,849,320. The following treatments are evaluated:
A. Seed coated with an intimate mixture of the bacterial spores and the germinative compound
B. Seed coated with a conventional mixture of the bacterial spores and the germinative compound
C. Seed coated with the bacterial spores alone
D. Uncoated seed Seed germination rates are measured in greenhouse and field trials by measuring seedling emergence each day beginning on the first day that plants emerge and continuing for three weeks after the first date of emergence. Yield is measured by harvesting the mature ears and drying them for three days in an oven at 37° C. The ears are then threshed and the seeds are collected and counted. Total seed weight is also measured by weighing the seed harvested from each plant.

Example 17: Effect of a Bacillus Probiotic in Chickens Infected with Eimeria maxima and Clostridium perfringens A 28-day battery test was performed on Cobb 500 Chicks (Gallus gallus domesticus) to determine the effect of supplementing feed with Bacillus probiotic agents or a standard antibiotic treatment (Bacitracin) on chickens infected with Eimeria maxima (a causative agent of coccidiosis in poultry) and Clostridium prefringens (a causative agent of necrotic enteritis). The Bacillus probiotic contained equal ratios of Bacillus subtilis, Bacillus licheniformis and Bacillus pumilis. A GO+Bacillus probiotic was prepared by spray drying spores of the Bacillus species with L-alanine. L-alanine was introduced to the spore mass immediately prior to spray drying as a solution containing 0.044 grams of alanine per milliliter of distilled water as described above. A GO−Bacillus probiotic was formed by spray drying spores of the Bacillus species without addition of L-alanine, as described above. The study included eight replicate cages for each treatment group with eight chicks to a cage (64 birds per treatment group). The following treatment groups were evaluated. Treatment groups 2-5 were infected with Eimeria maxima and Clostridium prefringens (infected). Treatment group 1 was not infected with Eimeria maxima or Clostridium prefringens to serve as an uninfected negative control.
1) No feed additive, no infection (uninfected negative control)
2) No feed additive, infected (infected negative control)
3) GO− Bacillus probiotic, $2 \times 10^6$ cfu/g of feed, infected
4) GO+Bacillus probiotic, $2 \times 10^6$ cfu/g of feed, infected
5) antibiotic Bacitracin, 50 g/ton of feed, infected (positive control)

The chickens were fed with the treated or untreated feed starting on Day 0. On Day 14 the birds in treatment groups 2-5 were stressed with an infection of Eimeria maxima followed by infection with Clostridium perfringens, a causative agent of necrotic enteritis. The birds were evaluated for feed conversion, weight gain, lesion score and percent mortality on Day 28. Feed conversion was calculated as the ratio of the kg of food required to produce a kg of body weight from Day 0 to Day 28. For example, a feed conversion of 1.6 means that 1.6 kg of food were required to produce 1 kg of body weight. Weight gain was measured as the increase in body weight from Day 0 to Day 28. Lesion score was based on visual observation of lesions, with 0 being normal and 3 being the most severe. Both GO− and GO+ Bacillus probiotics reduced percent mortality over the infected negative control (treatment group 2). See Table 18.

Percent mortality was lower in the chicks treated with GO+ probiotic treatment compared to those treated with Bacitracin, but the difference was not statistically significant. Both GO+ probiotic and antibiotic treatment groups exhibited a significant increase in weight gain over the infected negative control. These results indicate that treatment of chicken feed with GO+ probiotics achieved the same or better results compared to the standard antibiotic treatment during pathogen challenge.

TABLE 18

Feed conversion, weight gain, lesion score and percent mortality in chickens infected with *Eimeria maxima* and *Clostridium perfringens* (treatment groups 2-5) or in uninfected negative control (treatment group 1). The treatment groups are described above. Letters following the values represent statistically significant differences among treatment groups.

| Treatment Group | Feed Conversion Day 0-28 | Weight Gain (kg) Day 0-28 | Lesion Score (0-3) | Mortality (%) |
|---|---|---|---|---|
| 1 | 1.600bc | 0.805a | 0.0c | 0.0b |
| 2 | 1.913a | 0.696c | 0.8a | 14.1a |
| 3 | 1.707b | 0.726bc | 0.2c | 3.1b |
| 4 | 1.691bc | 0.755ab | 0.5b | 1.6b |
| 5 | 1.585c | 0.811a | 0.5b | 3.1b |

Example 18: Effect of Probiotics on Clams Infected with *Vibrio* Species

A bivalve hatchery in Florida experiencing larvae die-off events was evaluated for the cause of the die-off by isolating and quantifying the bacterial load in the hatchery. It was determined that *Vibrio* species accounted for 100% of the aerobic counts ($4 \times 10^4$ cfu/ml) found in the source water, and approx. 50% of the aerobic counts ($2 \times 10^4$ cfu/ml) in the hatchery. Of this large *Vibrio* population, two dominant colony morphologies over different media were found and sent for identification. The two dominant *Vibrio* strains observed were *Vibrio* chagasii and *Vibrio coralliilyticus*, the latter of which has been shown to be virulent against bivalves.

Measurement of exclusion zones for individual strains of *Bacillus licheniformis*, *Bacillus subtilis*, and *Bacillus pumilus* on *Vibrio* growth and restriction of biofilm formation indicated that these *Bacillus* strains were found to have moderate to good activity against most of the *Vibrio* strains tested. These results indicate that the *Bacillus* strains outperformed strains of *Vibrio* species isolated from the hatchery in biofilm formation and had a direct effect against the *Vibrio* biofilms.

The clam larvae tanks infected with the *Vibrio* strains were treated with a 4 strain probiotic blend containing equal ratios of two strains of *Bacillus licheniformis*, one strain of *Bacillus subtilis* and one strain of *Bacillus pumilis*. The *Bacillus* strains were formulated by spray drying as either GO+(with L-alanine) or GO− (without L-alanine) as described above. The probiotics were added to the tanks by suspending the spray dried formulation in 1 liter of water and then adding the suspension immediately to the tank after the daily water changes at a dose of $5 \times 10^5$ cfu/ml. The clam larvae were sieved on different size mesh filters (150, 200, 250 or 300 µm) at the beginning of the treatment period and 12 days after daily treatment began. On Day 12, the number of live clam larvae found on each screen size was recorded relative to the starting number of larvae. See Table 19.

During the die-off event in clams, the untreated tank only had a ~10% survival rate whereas the GO− treated tank had ~20% survival, and the GO+ treated tank had ~40% survival. Additionally the probiotic treatments increased the growth rate (more larvae collected on larger screens) with GO+ treated tanks growing the fastest.

TABLE 19

Percent survival rate of clam larvae of various sizes after 12 days of treatment with probiotic. The clam larvae tanks were infected with *Vibrio* strains.

| | Mesh Size | | | | |
|---|---|---|---|---|---|
| | 150 µm | 200 µm | 250 µm | 300 µm | Total |
| Control | 3.75 | 2 | 5 | 0 | 10.75 |
| Envera GO− | 0 | 10 | 9.9 | 1 | 20.9 |
| Envera GO+ | 3 | 6 | 20 | 10 | 39 |

Example 19: Biological Oxygen Demand (BOD) Determination in a Closed System Evaluating Formulations of *Bacillus licheniformis* in Chicken Feed Extracts with Bile Salts Bacterial Oxygen Demand (BOD) of *Bacillus licheniformis* was measured in chicken feed extracts supplemented with bile salts to determine the ability of the bacteria to grow under bile salt stress. Chicken feed was used as the energy source in combination with 4 mM bile salts (60% taurodeoxycholate, 30% glycodeoxycholate, 10% deoxycholate).
Medium: Preparation of Chicken Feed Extract Supplemented with Bile Salts 42.44 g of chicken feed (Chick Starter Grower) was weighed into a beaker and then ground into powder using a coffee grinder. The volume was brought to a total of 1 Liter with warm tap water, and the mixtures was mixed on a stir plate for 60 minutes. 100 mls of the solution was dispensed into 250 mL baffled shake flasks, including 2 "preliminary test flasks" and autoclaved.
Bile Salt Stock Solution (BSSS):
1. 1.8 g taurodeoxycholate
2. 0.9 g glycodeoxycholate
3. 0.3 g deoxycholate Each component was mixed separately in small amounts of tap water until just dissolved and then the solutions were mixed together, brought up to 30 mL, and filter sterilized.

A 1.0 N Solution of HCl was prepared and added to the preliminary test flasks described above to reduce the pH to 2.25. The volume of HCl used to reduce the pH was recorded. After exactly 90 minutes, the pH was recorded (the pH rose during this time). 1.6 ml of BSSS was added to each flask. After 15 minutes, the pH was increased to 7.5 using 1.0 M NaOH. The volume of NaOH used was recorded. After 15 minutes, the pH was recorded (the pH fell during this time span). The results were averaged and the amounts were used to treat the remaining flasks containing chicken feed extract.
Spore Suspensions:

Spore powders of *Bacillus licheniformis* strain ENV100 prepared as GO+(spray dried with L-alanine as described above) or GO− (spray dried without L-alanine as described above) formulations were prepared. The formulations were suspended in sterile water with 0.1% Octosol SLS (FT-SLS-246DRUM, Tiarco Chemical, Dalton, Ga.) within a sterile blender jar. Spores were suspended by blending for 5 second intervals for a total of at least 15 seconds or until the spores were completely suspended visually followed by serial dilutions in sterile water. This was performed such that the final concentration in the BOD bottles was $5 \times 10^7$ cfu/ml or $5 \times 10^3$ cfu/ml.

BOD Assay:

Biological Oxygen Demand (BOD) was measured on BODTRAKII instruments (Hach 2952450) according to manufacturer's instructions. 2 ml of the prepared chicken feed extract containing bile salts described above was added to 98 ml water in BOD bottles, autoclaved, and allowed to cool to room temperature. The BODTRAKII instruments and bottles were preincubated at 37° C. before inoculation. Bottles were inoculated as described above, and immediately closed according to manufacturer's instructions, and incubated at 37° C. After the assay was complete, the data was downloaded from the instrument and approximately 10 μl of the culture was streaked to PCA plates to test for purity.

As shown in Table 20, the GO+ formulation of *Bacillus licheniformis* spores enabled growth in bile salt stress conditions and resulted in increased metabolism (as measured by Biological Oxygen Demand) versus a control treatment. These data demonstrate that the GO+ formulation improves *Bacillus licheniformis* growth under bile stress conditions.

TABLE 20

Biological Oxygen Demand (BOD) measurement expressed as amount of Oxygen utilized (mg/L) in *Bacillus licheniformis* cultures containing chicken feed extract and bile salts.

| | *Bacillus licheniformis* concentration | | | |
| --- | --- | --- | --- | --- |
| | $5 \times 10^7$ cfu/ml | | $5 \times 10^3$ cfu/ml | |
| Days | GO+ 7 logs | GO− 7 logs | GO+ 3 logs | GO− 3 logs |
| 0 | 0 | 0 | 0 | 0 |
| 0.22 | 1.7 | −2.5 | −1.8 | −1.5 |
| 0.5 | 12 | −2 | −2.3 | −2.1 |
| 0.75 | 17 | 6.5 | −1.4 | −1.1 |
| 1.03 | 19 | 14 | −0.7 | −0.5 |
| 1.56 | 19 | 16 | 5.9 | −1 |
| 1.75 | 21 | 19 | 13 | 3 |
| 2 | 20 | 18 | 16 | 11 |
| 2.25 | 20 | 18 | 18 | 16 |
| 2.5 | 21 | 19 | 21 | 19 |
| 2.75 | 22 | 20 | 23 | 21 |
| 3 | 21 | 20 | 22 | 21 |

What is claimed is:

1. A method for feeding an animal in an aquaculture system, comprising administering an animal feed comprising a spray-dried mixture comprising a bacterial spore and a germinative compound to the animal in the aquaculture system, wherein the spray-dried mixture is prepared by spray-drying a solution comprising the germinative compound and the bacterial spore, wherein the germinative compound is adsorbed to or adsorbed by the bacterial spore and binds to said bacterial spore's germination initiator sites when the mixture reaches an appropriate environment for germination, and wherein the germinative compound is an L-amino acid.

2. The method of claim 1, wherein the bacterial spore is selected from the group consisting of *Bacillus agri, Bacillus thurengiensis* var. *aizawai, Bacillus albolactis, Bacillus altitudinis, Bacillus amyloliquefaciens, Bacillus butanolivorans, Bacillus cereus, Bacillus coagulans, Bacillus licheniformis* var. *endoparasiticus, Bacillus endorhythmos, Bacillus firmus, Bacillus thuringiensis* var. *kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus papillae, Bacillus pumilus, Bacillus siamensis, Bacillus simplex, Bacillus sphaericus, Bacillus* spp., *Bacillus subtilis, Bacillus thuringiensis,* and *Bacillus unifagellatus.*

3. The method of claim 1, wherein the germinative compound is selected from the group consisting of L-alanine, L-valine, L-proline, L-leucine, L-cysteine, L-threonine, L-glutamine, L-asparagine, L-phenylalanine and analogues thereof.

4. The method of claim 1, wherein the bacterial spore is selected from the group consisting of *B. subtilis, B. amyloliquefaciens, B. firmus, B. licheniformis, B. megaterium,* and *B. pumilus*; and the germinative compound is selected from the group consisting of L-alanine, L-valine and L-asparagine.

5. The method of claim 4, wherein the composition is in the form of a dry powder.

6. The method of claim 1, wherein the composition is in the form of an emulsion.

7. The method of claim 1, Wherein the germinative compound is L-alanine.

8. A method for feeding an animal comprising administering a composition comprising a spray-dried mixture comprising a bacterial spore and a germinative compound to the animal, wherein the spray-dried mixture is prepared by spray-drying a solution comprising the germinative compound and the bacterial spore, wherein the germinative compound is adsorbed to or adsorbed by the bacterial spore and binds to said bacterial spore's germination initiator sites when the mixture reaches an appropriate environment for germination, and wherein the germinative compound is an L-amino acid.

9. The method of claim 8, wherein the bacterial spore is selected from the group consisting of *Bacillus agri, Bacillus thuringiensis* var. *aizawai, Bacillus albolactis, Bacillus altitudinis, Bacillus amyloliquefaciens, Bacillus butanolivorans, Bacillus cereus, Bacillus coagulans, Bacillus licheniformis* var. *endoparasiticus, Bacillus endorhythmos, Bacillus firmus, Bacillus thuringiensis* var. *kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus mojavensis, Bacillus mycoides, Bacillus natto, Bacillus nigrificans, Bacillus papillae, Bacillus pumilus, Bacillus siamensis, Bacillus simplex, Bacillus sphaericus, Bacillus* spp., *Bacillus subtilis, Bacillus thuringiensis,* and *Bacillus unifagellatus.*

10. The method of claim 8, wherein the germinative compound is selected from the group consisting of L-alanine, L-valine, L-proline, L-leucine, L-cysteine, L-threonine, L-asparagine, L-phenylalanine and analogues thereof.

11. The method of claim 8, wherein the bacterial spore is selected from the group consisting of *B. subtilis, B. amyloliquefaciens, B. firmus, B. licheniformis, B. megaterium,* and *B. pumilus*; and the germinative compound is selected from the group consisting of L-alanine, L-valine and L-asparagine.

12. The method of claim 8, wherein the composition is in the form of a dry powder.

13. The method of claim 8, wherein the composition is in the form of an emulsion.

14. The method of claim 8, wherein the germinative compound is L-alanine.

\* \* \* \* \*